(12) United States Patent
Demmer et al.

(10) Patent No.: US 8,718,770 B2
(45) Date of Patent: May 6, 2014

(54) CAPTURE THRESHOLD MEASUREMENT FOR SELECTION OF PACING VECTOR

(75) Inventors: Wade M. Demmer, Coon Rapids, MN (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 631 days.

(21) Appl. No.: 12/909,057

(22) Filed: Oct. 21, 2010

(65) Prior Publication Data
US 2012/0101543 A1 Apr. 26, 2012

(51) Int. Cl.
*A61N 1/08* (2006.01)

(52) U.S. Cl.
USPC .......................................................... 607/28

(58) Field of Classification Search
None
See application file for complete search history.

(56) References Cited

U.S. PATENT DOCUMENTS

| | | | |
|---|---|---|---|
| 2,956,586 | A | 10/1960 | Zeigler et al. |
| 3,857,399 | A | 12/1974 | Zacouto |
| 3,888,260 | A | 6/1975 | Fischell |
| 3,985,123 | A | 10/1976 | Herzlinger et al. |
| 4,164,946 | A | 8/1979 | Langer |
| 4,262,982 | A | 4/1981 | Kenny |
| 4,397,314 | A | 8/1983 | Vaguine |
| 4,399,820 | A | 8/1983 | Wirtzfield et al. |
| 4,600,454 | A | 7/1986 | Plummer |
| 4,603,705 | A | 8/1986 | Speicher et al. |
| 4,628,934 | A | 12/1986 | Pohndorf et al. |
| 4,628,935 | A | 12/1986 | Jones et al. |
| 4,750,494 | A | 6/1988 | King |
| 4,776,334 | A | 10/1988 | Prionas |
| 4,877,032 | A | 10/1989 | Heinze et al. |
| 4,878,898 | A | 11/1989 | Griffin et al. |
| 4,881,410 | A | 11/1989 | Wise et al. |
| 4,902,273 | A | 2/1990 | Choy et al. |
| 5,004,275 | A | 4/1991 | Miller |

(Continued)

FOREIGN PATENT DOCUMENTS

| EP | 0659388 A1 | 6/1995 |
|---|---|---|
| EP | 1048321 A2 | 11/2000 |

(Continued)

OTHER PUBLICATIONS

Auricchio et al., "The Pacing Therapies for Congestive Heart Failure (PATH-CHF) Study: Rationale, Design and Endpoints of a Prospective Randomized Multicenter Study" Am J. Cardio., 83:130D-135D, 1999.

(Continued)

*Primary Examiner* — Brian T Gedeon
*Assistant Examiner* — Ankit Tejani
(74) *Attorney, Agent, or Firm* — Michael C. Soldner

(57) ABSTRACT

Various techniques for selecting a pacing vector based on pacing capture thresholds are described. One example method described includes for each of a plurality of vectors, iteratively delivering at least one pacing stimulus at each of a plurality of magnitudes within a predetermined range of magnitudes to a first chamber, determining if a depolarization occurred in a second chamber of the heart within a predetermined threshold time interval after the pacing stimulus that is less than an interval, identifying a pacing stimulus for which a depolarization in the second chamber does not occur within the predetermined threshold time interval, determining a capture threshold magnitude for the vector based on the magnitude of the pacing pulse for which a depolarization in the second chamber does not occur within the predetermined threshold time interval, and recording the capture threshold magnitudes.

25 Claims, 9 Drawing Sheets

(56) References Cited

U.S. PATENT DOCUMENTS

| | | |
|---|---|---|
| 5,005,613 A | 4/1991 | Stanley |
| 5,035,246 A | 7/1991 | Heuvelmans et al. |
| 5,111,816 A | 5/1992 | Pless et al. |
| 5,113,868 A | 5/1992 | Wise et al. |
| 5,156,154 A | 10/1992 | Valenta, Jr. et al. |
| 5,158,536 A | 10/1992 | Sekins et al. |
| 5,176,619 A | 1/1993 | Segalowitz |
| 5,188,106 A | 2/1993 | Nappholz et al. |
| 5,209,238 A | 5/1993 | Sundhar |
| 5,213,098 A | 5/1993 | Bennett et al. |
| 5,243,981 A | 9/1993 | Hudrlik |
| 5,285,744 A | 2/1994 | Grantham et al. |
| 5,305,745 A | 4/1994 | Zacouto |
| 5,313,020 A | 5/1994 | Sackett |
| 5,391,199 A | 2/1995 | Ben-Haim |
| 5,411,532 A | 5/1995 | Mortazavi |
| 5,411,537 A | 5/1995 | Munshi et al. |
| 5,417,717 A | 5/1995 | Salo et al. |
| 5,419,767 A | 5/1995 | Eggers et al. |
| 5,423,323 A | 6/1995 | Orth |
| 5,433,198 A | 7/1995 | Desai |
| 5,500,006 A | 3/1996 | Heinze |
| 5,509,411 A | 4/1996 | Littmann et al. |
| 5,535,752 A | 7/1996 | Halperin et al. |
| 5,544,656 A | 8/1996 | Pitsillides et al. |
| 5,549,650 A | 8/1996 | Bornzin et al. |
| 5,579,234 A | 11/1996 | Wiley et al. |
| 5,579,764 A | 12/1996 | Goldreyer |
| 5,591,142 A | 1/1997 | Van Erp |
| 5,593,430 A | 1/1997 | Renger |
| 5,628,777 A | 5/1997 | Moberg et al. |
| 5,662,587 A | 9/1997 | Grundfest et al. |
| 5,674,258 A | 10/1997 | Henschel et al. |
| 5,676,153 A | 10/1997 | Smith et al. |
| 5,683,429 A | 11/1997 | Mehra |
| 5,720,768 A | 2/1998 | Verboven-Nelissen |
| 5,743,267 A | 4/1998 | Nikolic et al. |
| 5,751,050 A | 5/1998 | Ishikawa et al. |
| 5,788,647 A | 8/1998 | Eggers |
| 5,797,903 A | 8/1998 | Swanson et al. |
| 5,800,460 A | 9/1998 | Powers et al. |
| 5,800,465 A | 9/1998 | Thompson et al. |
| 5,810,735 A | 9/1998 | Halperin et al. |
| 5,814,089 A | 9/1998 | Stokes et al. |
| 5,836,987 A | 11/1998 | Baumann et al. |
| 5,873,849 A | 2/1999 | Bernard |
| 5,902,234 A | 5/1999 | Webb |
| 5,902,248 A | 5/1999 | Millar et al. |
| 5,913,814 A | 6/1999 | Zantos |
| 5,924,997 A | 7/1999 | Campbell |
| 5,935,084 A | 8/1999 | Southworth |
| 5,938,690 A | 8/1999 | Law et al. |
| 5,941,904 A | 8/1999 | Johnston et al. |
| 5,957,957 A | 9/1999 | Sheldon |
| 5,999,848 A | 12/1999 | Gord et al. |
| 6,009,349 A | 12/1999 | Mouchawar et al. |
| 6,015,386 A | 1/2000 | Kensey et al. |
| 6,024,704 A | 2/2000 | Meador et al. |
| 6,032,699 A | 3/2000 | Cochran et al. |
| 6,033,398 A | 3/2000 | Farley et al. |
| 6,038,480 A | 3/2000 | Hrdlicka et al. |
| 6,044,297 A | 3/2000 | Sheldon et al. |
| 6,058,329 A | 5/2000 | Salo et al. |
| 6,061,593 A | 5/2000 | Fischell et al. |
| 6,077,136 A | 6/2000 | Arai et al. |
| 6,078,830 A | 6/2000 | Levin et al. |
| 6,081,748 A | 6/2000 | Struble et al. |
| 6,115,626 A | 9/2000 | Whayne et al. |
| 6,115,636 A | 9/2000 | Ryan |
| 6,120,442 A | 9/2000 | Hickey |
| 6,155,267 A | 12/2000 | Nelson |
| 6,163,716 A | 12/2000 | Edwards et al. |
| 6,163,725 A | 12/2000 | Peckham et al. |
| 6,165,135 A | 12/2000 | Neff |
| 6,171,252 B1 | 1/2001 | Roberts |
| 6,197,021 B1 | 3/2001 | Panescu et al. |
| 6,197,677 B1 | 3/2001 | Lee et al. |
| 6,206,835 B1 | 3/2001 | Spillman, Jr. et al. |
| 6,206,874 B1 | 3/2001 | Ubby et al. |
| 6,223,080 B1 | 4/2001 | Thompson |
| 6,234,973 B1 | 5/2001 | Meador et al. |
| 6,241,418 B1 | 6/2001 | Suzuki et al. |
| 6,264,606 B1 | 7/2001 | Ekwall et al. |
| 6,277,078 B1 | 8/2001 | Porat et al. |
| 6,287,256 B1 | 9/2001 | Park et al. |
| 6,299,582 B1 | 10/2001 | Brockway et al. |
| 6,301,500 B1 | 10/2001 | Van Herck et al. |
| 6,309,350 B1 | 10/2001 | VanTassel et al. |
| 6,309,385 B1 | 10/2001 | Simpson |
| 6,328,699 B1 | 12/2001 | Eigler et al. |
| 6,360,123 B1 | 3/2002 | Kimchi et al. |
| 6,363,279 B1 | 3/2002 | Ben-Haim et al. |
| 6,366,811 B1 | 4/2002 | Carlson |
| 6,370,431 B1 | 4/2002 | Stoop et al. |
| 6,406,677 B1 | 6/2002 | Carter et al. |
| 6,421,567 B1 | 7/2002 | Witte |
| 6,438,408 B1 | 8/2002 | Mulligan et al. |
| 6,466,820 B1 | 10/2002 | Juran et al. |
| 6,477,395 B2 | 11/2002 | Schulman et al. |
| 6,477,417 B1 | 11/2002 | Levine |
| 6,484,727 B1 | 11/2002 | Vaska et al. |
| 6,496,730 B1 | 12/2002 | Kleckner et al. |
| 6,580,946 B2 | 6/2003 | Struble |
| 6,584,362 B1 | 6/2003 | Scheiner et al. |
| 6,600,954 B2 | 7/2003 | Cohen et al. |
| 6,611,714 B1 | 8/2003 | Mo |
| 6,618,619 B1 | 9/2003 | Florio et al. |
| 6,628,989 B1 | 9/2003 | Penner et al. |
| 6,640,136 B1 * | 10/2003 | Helland et al. ............... 607/28 |
| 6,666,826 B2 | 12/2003 | Salo et al. |
| 6,768,924 B2 | 7/2004 | Ding et al. |
| 6,812,796 B2 | 11/2004 | Pryanishnikov et al. |
| 6,885,889 B2 | 4/2005 | Chinchoy |
| 6,885,893 B1 | 4/2005 | Lu |
| 6,934,584 B1 | 8/2005 | Wong et al. |
| 6,978,184 B1 | 12/2005 | Marcus et al. |
| 6,993,384 B2 | 1/2006 | Bradley et al. |
| 6,994,676 B2 | 2/2006 | Mulligan et al. |
| 7,020,524 B1 | 3/2006 | Bradley |
| 7,047,084 B2 | 5/2006 | Erickson et al. |
| 7,174,218 B1 | 2/2007 | Kuzma |
| 7,200,437 B1 | 4/2007 | Nabutovsky et al. |
| 7,200,439 B2 | 4/2007 | Zdeblick et al. |
| 7,204,798 B2 | 4/2007 | Zdeblick et al. |
| 7,214,189 B2 | 5/2007 | Zdeblick |
| 7,267,649 B2 | 9/2007 | Zdeblick et al. |
| 7,392,088 B2 | 6/2008 | Dong et al. |
| 7,426,412 B1 * | 9/2008 | Schecter ............... 607/20 |
| 7,467,016 B2 | 12/2008 | Colborn |
| 7,561,914 B2 | 7/2009 | Busacker et al. |
| 7,574,259 B1 | 8/2009 | Pei et al. |
| 7,583,998 B2 | 9/2009 | Meyer et al. |
| 7,640,060 B2 | 12/2009 | Zdeblick |
| 7,680,536 B2 | 3/2010 | Sathaye et al. |
| 7,684,863 B2 | 3/2010 | Parikh et al. |
| 7,792,585 B1 | 9/2010 | Shelchuk |
| 2001/0000187 A1 | 4/2001 | Peckham et al. |
| 2001/0002924 A1 | 6/2001 | Tajima |
| 2001/0025192 A1 | 9/2001 | Gerber et al. |
| 2001/0047138 A1 | 11/2001 | Kokate et al. |
| 2001/0053882 A1 | 12/2001 | Haddock et al. |
| 2002/0026183 A1 | 2/2002 | Simpson |
| 2002/0040236 A1 | 4/2002 | Lau et al. |
| 2002/0045921 A1 | 4/2002 | Wolinsky et al. |
| 2002/0072656 A1 | 6/2002 | Vantassel et al. |
| 2002/0077568 A1 | 6/2002 | Haddock |
| 2002/0077673 A1 | 6/2002 | Penner et al. |
| 2002/0095196 A1 | 7/2002 | Linberg |
| 2002/0099419 A1 | 7/2002 | Cohen et al. |
| 2002/0111560 A1 | 8/2002 | Kokate et al. |
| 2002/0120186 A1 | 8/2002 | Keimel |
| 2002/0151816 A1 | 10/2002 | Rich et al. |
| 2002/0156417 A1 | 10/2002 | Rich et al. |
| 2002/0161307 A1 | 10/2002 | Yu et al. |

(56) References Cited

U.S. PATENT DOCUMENTS

| | | |
|---|---|---|
| 2002/0169445 A1 | 11/2002 | Jain et al. |
| 2002/0193859 A1 | 12/2002 | Schulman et al. |
| 2003/0078623 A1 | 4/2003 | Weinberg et al. |
| 2003/0105496 A1 | 6/2003 | Yu et al. |
| 2003/0153952 A1 | 8/2003 | Auricchio et al. |
| 2003/0191502 A1 | 10/2003 | Sharma et al. |
| 2004/0024440 A1 | 2/2004 | Cole |
| 2004/0039417 A1 | 2/2004 | Soykan et al. |
| 2004/0093053 A1 | 5/2004 | Gerber et al. |
| 2004/0097965 A1 | 5/2004 | Gardeski et al. |
| 2004/0098074 A1 | 5/2004 | Erickson et al. |
| 2004/0143154 A1 | 7/2004 | Lau et al. |
| 2004/0193021 A1 | 9/2004 | Zdeblick et al. |
| 2004/0199235 A1 | 10/2004 | Younis |
| 2004/0215049 A1 | 10/2004 | Zdeblick et al. |
| 2004/0220637 A1 | 11/2004 | Zdeblick et al. |
| 2004/0254483 A1 | 12/2004 | Zdeblick et al. |
| 2004/0260346 A1 | 12/2004 | Overall et al. |
| 2005/0027320 A1 | 2/2005 | Nehls et al. |
| 2005/0054892 A1 | 3/2005 | Lau et al. |
| 2005/0102011 A1 | 5/2005 | Lau et al. |
| 2005/0246004 A1 | 11/2005 | Cameron et al. |
| 2005/0267542 A1 | 12/2005 | David et al. |
| 2006/0058588 A1 | 3/2006 | Zdeblick |
| 2006/0074454 A1 | 4/2006 | Freeberg |
| 2006/0122678 A1 | 6/2006 | Olsen et al. |
| 2006/0161211 A1 | 7/2006 | Thompson et al. |
| 2006/0247539 A1 | 11/2006 | Schugt et al. |
| 2006/0265038 A1 | 11/2006 | Hagen et al. |
| 2006/0287685 A1 | 12/2006 | Meyer et al. |
| 2007/0100399 A1 | 5/2007 | Parramon et al. |
| 2007/0123944 A1 | 5/2007 | Zdeblick |
| 2007/0172896 A1 | 7/2007 | Goueli et al. |
| 2007/0179569 A1 | 8/2007 | Zdeblick |
| 2007/0198066 A1 | 8/2007 | Greenberg et al. |
| 2007/0203517 A1 | 8/2007 | Williams et al. |
| 2007/0219591 A1 | 9/2007 | Zdeblick et al. |
| 2007/0219608 A1 | 9/2007 | Swoyer et al. |
| 2007/0255336 A1 | 11/2007 | Herbert et al. |
| 2007/0255373 A1 | 11/2007 | Metzler et al. |
| 2007/0255460 A1 | 11/2007 | Lopata |
| 2008/0007186 A1 | 1/2008 | Lu et al. |
| 2008/0021292 A1 | 1/2008 | Stypulkowski |
| 2008/0027289 A1 | 1/2008 | Zdeblick |
| 2008/0039916 A1 | 2/2008 | Colliou et al. |
| 2008/0045826 A1 | 2/2008 | Greenberg et al. |
| 2008/0058656 A1 | 3/2008 | Costello et al. |
| 2008/0061630 A1 | 3/2008 | Andreu et al. |
| 2008/0091246 A1 | 4/2008 | Carey et al. |
| 2008/0097227 A1 | 4/2008 | Zdeblick et al. |
| 2008/0097566 A1 | 4/2008 | Colliou |
| 2008/0114230 A1 | 5/2008 | Addis |
| 2008/0140141 A1 | 6/2008 | Ben-David et al. |
| 2008/0140167 A1 | 6/2008 | Hagen et al. |
| 2008/0147168 A1 | 6/2008 | Ransbury et al. |
| 2008/0154328 A1 | 6/2008 | Thompson et al. |
| 2008/0167702 A1 | 7/2008 | Ransbury et al. |
| 2008/0177343 A1 | 7/2008 | Dal Molin et al. |
| 2008/0255647 A1 | 10/2008 | Jensen et al. |
| 2008/0294062 A1 | 11/2008 | Rapoport et al. |
| 2008/0294218 A1 | 11/2008 | Savage et al. |
| 2008/0306394 A1 | 12/2008 | Zdeblick et al. |
| 2008/0312726 A1 | 12/2008 | Frank et al. |
| 2009/0018632 A1 | 1/2009 | Zdeblick et al. |
| 2009/0024184 A1 | 1/2009 | Sun et al. |
| 2009/0043352 A1 | 2/2009 | Brooke et al. |
| 2009/0054946 A1 | 2/2009 | Sommer et al. |
| 2009/0054947 A1 | 2/2009 | Bourn et al. |
| 2009/0062880 A1 | 3/2009 | Li et al. |
| 2009/0287266 A1 | 11/2009 | Zdeblick |
| 2009/0299447 A1 | 12/2009 | Jensen et al. |
| 2010/0016928 A1 | 1/2010 | Zdeblick et al. |
| 2010/0137935 A1 | 6/2010 | Parikh et al. |
| 2010/0152801 A1 | 6/2010 | Koh et al. |
| 2010/0198292 A1* | 8/2010 | Honeck et al. .................. 607/17 |
| 2010/0204766 A1 | 8/2010 | Zdeblick et al. |
| 2011/0004264 A1 | 1/2011 | Siejko et al. |

FOREIGN PATENT DOCUMENTS

| | | |
|---|---|---|
| EP | 1050265 A2 | 11/2000 |
| EP | 1136033 A1 | 9/2001 |
| EP | 1266606 A2 | 12/2002 |
| EP | 1321097 A2 | 6/2003 |
| EP | 1426079 A2 | 6/2004 |
| EP | 1938861 A1 | 7/2008 |
| JP | 6456031 | 2/1989 |
| JP | 2099036 | 4/1990 |
| JP | 3055032 | 3/1991 |
| JP | 5269136 | 10/1993 |
| JP | 2000139833 | 5/2000 |
| JP | 2002272758 | 9/2002 |
| WO | WO 99/52588 A1 | 10/1999 |
| WO | WO 01/43821 A1 | 6/2001 |
| WO | WO 01/95787 A2 | 12/2001 |
| WO | WO 02/053228 A1 | 7/2002 |
| WO | WO 02/065894 A2 | 8/2002 |
| WO | WO 2004/020040 A2 | 3/2004 |
| WO | WO 2004/052182 A2 | 6/2004 |
| WO | WO 2004/066814 A2 | 8/2004 |
| WO | WO 2004/066817 A2 | 8/2004 |
| WO | WO 2004/067081 A2 | 8/2004 |
| WO | WO 2006/029090 A2 | 3/2006 |
| WO | WO 2006/042039 A2 | 4/2006 |
| WO | WO 2006/069322 A2 | 6/2006 |
| WO | WO 2006/073915 A2 | 7/2006 |
| WO | WO 2006/105474 A2 | 10/2006 |
| WO | WO 2007/005641 A2 | 1/2007 |
| WO | WO 2007/075974 A2 | 7/2007 |
| WO | WO 2007/120884 A2 | 10/2007 |
| WO | WO 2007/149546 A2 | 12/2007 |
| WO | WO 2008/004010 A2 | 1/2008 |
| WO | WO 2008/008755 A1 | 1/2008 |
| WO | WO 2008/027639 A2 | 3/2008 |
| WO | WO 2009/131749 A2 | 10/2009 |
| WO | 2010088355 A1 | 8/2010 |
| WO | 2011002671 A1 | 1/2011 |

OTHER PUBLICATIONS

Borky et al., "Integrated Signal Conditioning for Silicon Pressure Sensors" IEEE Transactions on Electron Devices ED-26(12): 1906-1910, 1979.

Little et al., "The Output of the Heart and its Control" Physiology of the Heart and Circulation, 4$^{th}$ ed., Year Book Medical Publishers Inc. pp. 165-187, 1989.

Paolocci et al., "Positive Inotropic ad Lusitropic Effects of HNO/NO in failing hearts: Independence from B-adrenergic signaling" PNAS vol. 100, No. 9, pp. 5537-5542, 2003.

Receveur et al., "Laterally Moving Bistable MEMS DC-Switch for Biomedical Applications," Journal of Microelectromechanical Systems, vol. 14, No. 5, Oct. 2005.

U.S. Appl. No. 12/893,517, by Elizabeth A. Schotzko, filed Sep. 9, 2010.

U.S. Appl. No. 12/395,538, by Bi et al., filed on Feb. 27, 2009.

International Search Report and Written Opinion of international application No. PCT/US2011/033551, dated Aug. 19, 2011, 12 pp.

International Preliminary Report on Patentability for Application Serial No. PCT/US2011/033551 dated May 2, 2013 (8 pages).

* cited by examiner

US 8,718,770 B2

CAPTURE THRESHOLD MEASUREMENT FOR SELECTION OF PACING VECTOR

TECHNICAL FIELD

This disclosure relates to implantable medical devices, and more particularly, to implantable medical devices that deliver cardiac pacing.

BACKGROUND

A wide variety of implantable medical devices for delivering a therapy or monitoring a physiologic condition have been clinically implanted or proposed for clinical implantation in patients. In some cases, implantable medical devices (IMD) deliver electrical stimulation therapy and/or monitor physiological signals via one or more electrodes or sensor elements, which may be included as part of one or more elongated implantable medical leads. Implantable medical leads may be configured to allow electrodes or sensors to be positioned at desired locations for sensing or delivery of stimulation. For example, electrodes or sensors may be carried at a distal portion of the lead. A proximal portion of the lead that may be coupled to an implantable medical device housing, which may contain electronic circuitry such as stimulation generation and/or sensing circuitry.

For example, implantable medical devices, such as cardiac pacemakers or implantable cardioverter defibrillators, provide therapeutic stimulation to the heart by delivering electrical therapy signals, such as pulses for pacing, or shocks for cardioversion or defibrillation, via electrodes of one or more implantable leads. In some cases, such an implantable medical device may sense for intrinsic depolarizations of the heart, and control the delivery of such signals to the heart based on the sensing. When an abnormal rhythm is detected, which may be bradycardia, tachycardia or fibrillation, an appropriate electrical signal or signals may be delivered to restore the normal rhythm. For example, in some cases, an implantable medical device may deliver pacing, cardioversion or defibrillation signals to the heart of the patient upon detecting ventricular tachycardia, and deliver defibrillation electrical signals to a patient's heart upon detecting ventricular fibrillation. Pacing signals typically have a lower energy than the cardioversion or defibrillation signals.

Patients with heart failure are, in some cases, treated with cardiac resynchronization therapy (CRT). CRT is a form of cardiac pacing. In some examples, CRT involves delivery of pacing pulses to both ventricles to synchronize their contraction. In other examples, CRT involves delivery of pacing pulses to one ventricle to synchronize its contraction with that of the other ventricular, such as pacing the left ventricle to synchronize its contraction with that of the right ventricle. CRT is one example of a variety of modes of cardiac pacing in which stimulation is delivered to one chamber or location at a time that is an interval before or after an event at another chamber or location. The event at the other chamber or location may be the delivery of a pacing pulse to the other chamber or location, or the detection of an intrinsic cardiac depolarization at the other chamber or location.

Various methods exist for detecting whether a pacing stimulus has captured the heart and determining capture thresholds. In some examples, a first pair of electrodes delivers a pacing pulse to a chamber, and the same or a different pair of electrodes detects an electrical signal, e.g., evoked response, in the chamber indicative of capture. In other examples, a device detects a mechanical contraction of the heart at the target site as evidence of capture of the heart by the pacing stimulus. In general, capture threshold determination or management involves delivery of pacing stimuli at incrementally increasing or decreasing magnitudes, e.g., voltage or current amplitudes or pulse widths, and identification of the magnitude at which capture or loss of capture occurs.

SUMMARY

In general, this disclosure is directed to techniques for determining pacing capture thresholds for each of a plurality of pacing vectors to facilitate selection of one of the pacing vectors. The pacing capture threshold determination techniques may include delivering pacing stimuli at various magnitudes, e.g., voltage amplitudes, to a first chamber of the heart, and, for each of the pacing stimuli, determining an interval between delivering the pacing stimuli and sensing of a subsequent depolarization in a second chamber of the heart. In some examples, the pacing stimuli are delivered to the left ventricle and the sensing of depolarizations is in the right ventricle. In such examples, the inter-chamber pace to sense interval determined for each pacing stimulus may be the left ventricle pace (LVP) to right ventricle sense (RVS) interval.

The length of the inter-chamber pace to sense interval may indicate whether the sensed event in the second (non-paced) chamber is the result of conduction of the pacing stimulus from the first chamber when the pacing stimulus captured the first chamber, or the result of intrinsic conduction when the pacing stimulus failed to capture the first chamber. In this manner, the length of the inter-chamber pace to sense interval indicates whether a pacing stimulus at a particular magnitude captured the first chamber. The techniques described herein may further include iteratively delivering pacing stimuli of various magnitudes, and determining a pacing stimulus magnitude at which capture/loss-of-capture (LOC) occurs based on the determined inter-chamber pace to sense intervals and/or evoked response information. In some cases, the pacing capture techniques of this disclosure may include pacing an atrium, measuring an intrinsic atrioventricular (AV) interval of a patient in response to the delivered pace, and determining an inter-ventricular pace to sense interval threshold based on the intrinsic AV interval.

Certain techniques of this disclosure provide an automated method for rapidly gathering information, such as, but not limited to, conduction time, evoked response, and/or impedance values, about a plurality of pacing vectors in order to aid a clinician in selecting the ideal vector. The techniques of this disclosure may include sequentially determining a pacing stimulus magnitude at which capture or loss of capture (LOC) occurs for each of a plurality of pacing vectors that are capable of pacing the first chamber, e.g., by sequentially testing a plurality of pacing vectors using the techniques described herein. The sequential testing of a plurality of vectors may be executed automatically, e.g., in response to a user command. A user may select a pacing vector having the lowest pacing magnitude at which capture or LOC occurred, or the pacing vector having the lowest pacing magnitude at which capture or LOC occurred may be selected automatically. Accordingly, using the techniques of this disclosure, a clinician or system may quickly determine one or more pacing vectors that have a low pacing threshold. The techniques described herein may be particularly advantageous for testing the plurality of pacing vectors available when a lead including more than two electrodes is implanted in or near a chamber, such as a left-ventricular pacing lead with four or more electrodes.

In one example, the disclosure is directed to a method of facilitating selection of at least one vector from among a plurality of vectors for pacing a first chamber of a heart. The method comprises, for each of the plurality of vectors, iteratively delivering at least one pacing stimulus at each of a plurality of magnitudes within a predetermined range of magnitudes to the first chamber, for each of the plurality of pacing stimuli, determining if a depolarization occurred in a second chamber of the heart within a predetermined threshold time interval after the pacing stimulus that is less than an intrinsic atrioventricular (AV) interval, identifying a pacing stimulus for which a depolarization in the second chamber does not occur within the predetermined threshold time interval, determining a capture threshold magnitude for the vector based on the magnitude of the pacing pulse for which a depolarization in the second chamber does not occur within the predetermined threshold time interval, and recording the capture threshold magnitudes for the plurality of vectors of the at least one of the vectors based on the capture threshold magnitudes.

In another example, the disclosure is directed to a system that facilitates selection of at least one vector from among a plurality of vectors for pacing a first chamber of a heart. The system comprises an implantable medical device configured to deliver pacing stimuli to the heart, and a capture detection module that, for each of the plurality of vectors, controls an implantable medical device to iteratively deliver at least one pacing stimulus at each of a plurality of magnitudes within a predetermined range of magnitudes to the first chamber, for each of the plurality of pacing stimuli, determines if a depolarization occurred in a second chamber of the heart within a predetermined threshold time interval after the pacing stimulus that is less than an intrinsic atrioventricular (AV) interval, identifies a pacing stimulus for which a depolarization in the second chamber does not occur within the predetermined threshold time interval, and determines a capture threshold magnitude for the vector based on the magnitude of the pacing stimulus for which a depolarization in the second chamber does not occur within the predetermined threshold time interval, wherein the capture detection module records the capture threshold magnitudes for the plurality of vectors for selection of one of the vectors based on the capture threshold magnitudes.

In another example, the disclosure is directed to a computer-readable storage medium comprising instructions that, when executed by a processor, cause the processor to control an implantable medical device to iteratively deliver at least one pacing stimulus at each of a plurality of magnitudes within a predetermined range of magnitudes to the first chamber, for each of the plurality of pacing stimuli, determine if a depolarization occurred in a second chamber of the heart within a predetermined threshold time interval after the pacing stimulus that is less than an intrinsic atrioventricular (AV) interval, identify a pacing stimulus for which a depolarization in the second chamber does not occur within the predetermined threshold time interval, and determine a capture threshold magnitude for the vector based on the magnitude of the pacing stimulus for which a depolarization in the second chamber does not occur within the predetermined threshold time interval, wherein the processor records the capture threshold magnitudes for the plurality of vectors for selection of one of the vectors based on the capture threshold magnitudes.

In another example, the disclosure is directed to a system comprising, for each of one or more vectors, means for delivering a first pacing pulse having a first voltage within a predetermined range of voltages to a left ventricle of a heart, the range of voltages having a maximum voltage and a minimum voltage, means for determining if depolarization occurred in a right ventricle of the heart within a time interval, if depolarization occurred in the right ventricle within the time interval, then through a first range of voltages between the first voltage and the minimum voltage, means for iteratively decreasing the first voltage and delivering a second pacing pulse to the left ventricle at one of the voltages in the first range until depolarization does not occur in the right ventricle within the time interval, and means for declaring loss of capture of the right ventricle if depolarization does not occur in the right ventricle, and if depolarization did not occur in the right ventricle within the time interval, then means for increasing the first voltage to the maximum value, through a second range of voltages between the maximum voltage and the first voltage, means for iteratively decreasing the maximum voltage and delivering a third pacing pulse to the left ventricle at one of the voltages in the third range until depolarization occurs in the right ventricle within the time interval, and means for declaring capture of the right ventricle if depolarization occurs in the right ventricle.

The details of one or more aspects of the disclosure are set forth in the accompanying drawings and the description below. Other features, objects, and advantages of the disclosure will be apparent from the description and drawings, and from the claims.

DETAILED DESCRIPTION

This disclosure describes techniques for measuring heart tissue pacing capture thresholds for a plurality of vectors to facilitate selection of one of the vectors based on the capture thresholds. The time interval between delivery of a pacing stimulus to a first chamber of a the heart and a subsequent depolarization of a second chamber of the heart may be useful in determining whether capture of the first chamber has occurred following the delivered pacing stimulus. For example, using various techniques of this disclosure, the time interval between a left ventricle (LV) pace and a right ventricle (RV) depolarization or sense (where no pacing pulse is delivered to the RV) may be used to determine whether the pacing stimulus captured the LV. Delivery of a pacing stimulus to the LV during a cardiac cycle without also delivering a pacing stimulus to the RV may be referred to as an LV-only pace or LV-only pacing.

Then, the LV pace (LVP) to RV sense (RVS) interval may be used to discriminate between capture and loss-of-capture (LOC). If the pacing pulse captured, then the magnitude, e.g., voltage amplitude, of the pacing pulse may be decreased until LOC is detected. If the pacing pulse did not capture, then the magnitude may be increased until capture occurs, then decremented until LOC occurs. In this manner, the techniques of this disclosure may quickly and accurately measure the estimated tissue pacing capture thresholds for one or more pacing vector configurations, thereby allowing a clinician to select particular vectors for the implantable medical device (IMD) that will deliver sufficient energy to pace the heart without unnecessarily depleting the battery.

Although the following description refers to examples in which a pacing pulse is delivered to the LV and depolarizations are sensed in the RV to determine an LVP-RVS interval, and whether the LVP captured the LV based on the LVP-RVS interval, it is to be understood that the disclosure is broadly applicable to any chambers of the heart being the stimulated chamber or sensing chamber, and to any type of stimulation. Furthermore, although described herein primarily with reference to examples in which voltage amplitude is adjusted during the test for a vector to identify a voltage amplitude at which capture/LOC occurs, the techniques are applicable to examples in which any one or more parameters that effects the magnitude of the pacing stimulus are adjusted.

Figure 1:
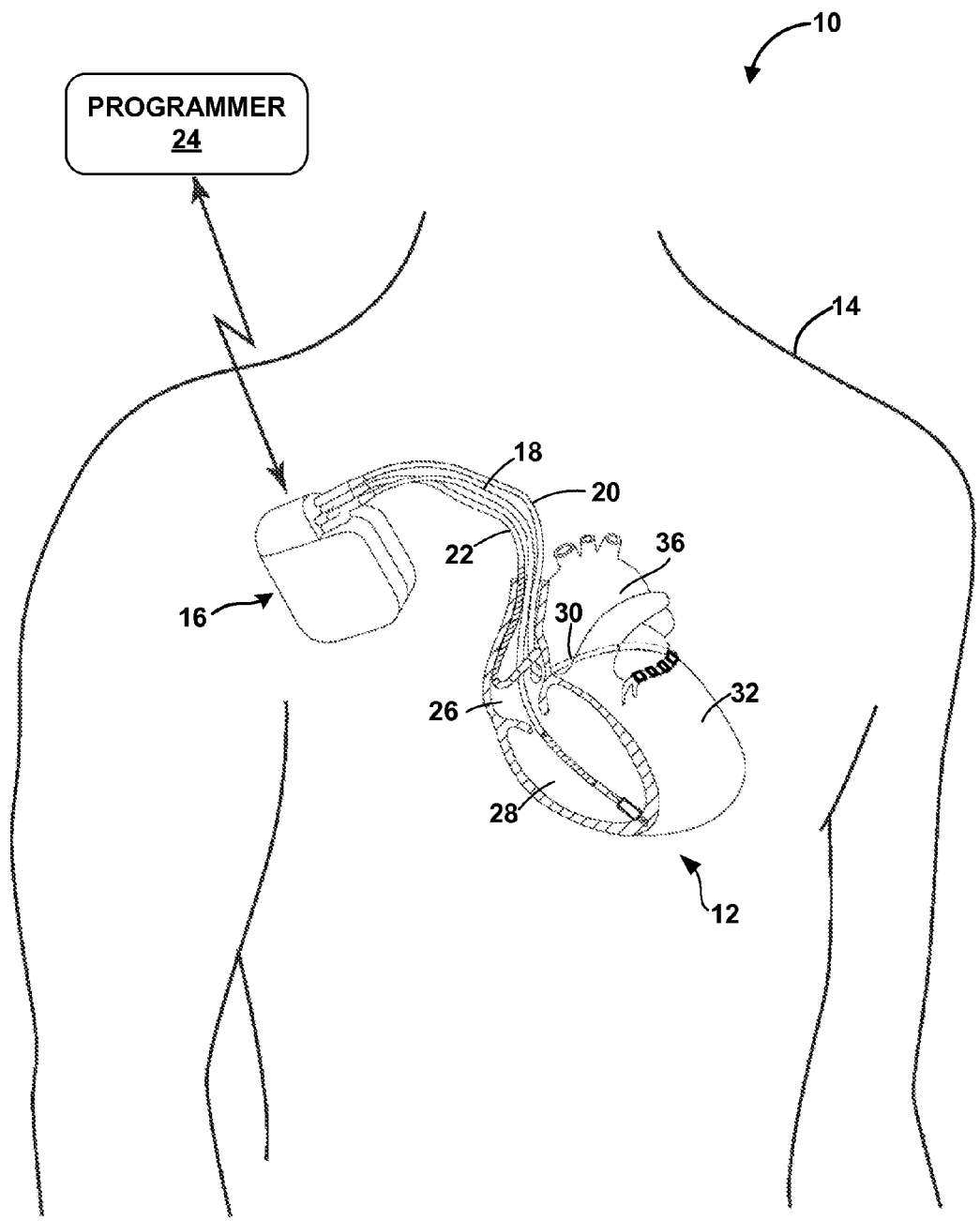
FIG. 1 is a conceptual diagram illustrating an example system that may be used to provide therapy to and/or monitor a heart of a patient.

FIG. 1 is a conceptual diagram illustrating an example system 10 that may be used to monitor and/or provide therapy to heart 12 of patient 14. Patient 14 ordinarily, but not necessarily, will be a human. System 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. In accordance with this disclosure, IMD 16 may deliver LV-only pacing pulses via a plurality of pacing vectors that include at least one electrode on lead 20 in order to assess LVP-RVS intervals to discriminate between capture and LOC, as will be described in greater detail below. IMD 16 may provide the measured intervals, data derived therefrom or alerts based thereon to programmer 24 via wireless telemetry.

Leads 18, 20, 22 extend into the heart 12 of patient 16 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 (shown in greater detail in FIG. 5) may be a handheld computing device or a computer workstation. A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20 and 22, or a power source of IMD 16. The user may use programmer 24 to program a therapy progression, select electrodes used to deliver defibrillation pulses, select waveforms for the defibrillation pulse, or select or configure a fibrillation detection algorithm for IMD 16. The user may also use programmer 24 to program aspects of other therapies provided by IMD 16, such as cardioversion or pacing therapies.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Using various techniques of this disclosure, IMD 16 may deliver LV-only pacing pulses via various combinations of electrodes that include at least one electrode on LV coronary sinus lead 20, for example. Subsequent to the delivery of each of the LV-only pacing pulses, electrical activity of the RV may be sensed by another combination of electrodes that includes at least one electrode on RV lead 18. If a depolarization of the right ventricular is sensed (RVS), the LVP-RVS interval may be determined. The intervals between the LVP and a RVS may be used to determine whether the LVP captured the LV. If the pacing pulse captured, then the amplitude of the voltage of the pacing pulse delivered via LV coronary sinus lead 20 may be decreased until LOC is detected. If the pacing pulse did not capture, then the amplitude of the pacing pulse may be increased until capture occurs, or decremented from a higher voltage value until LOC occurs.

Figure 2:
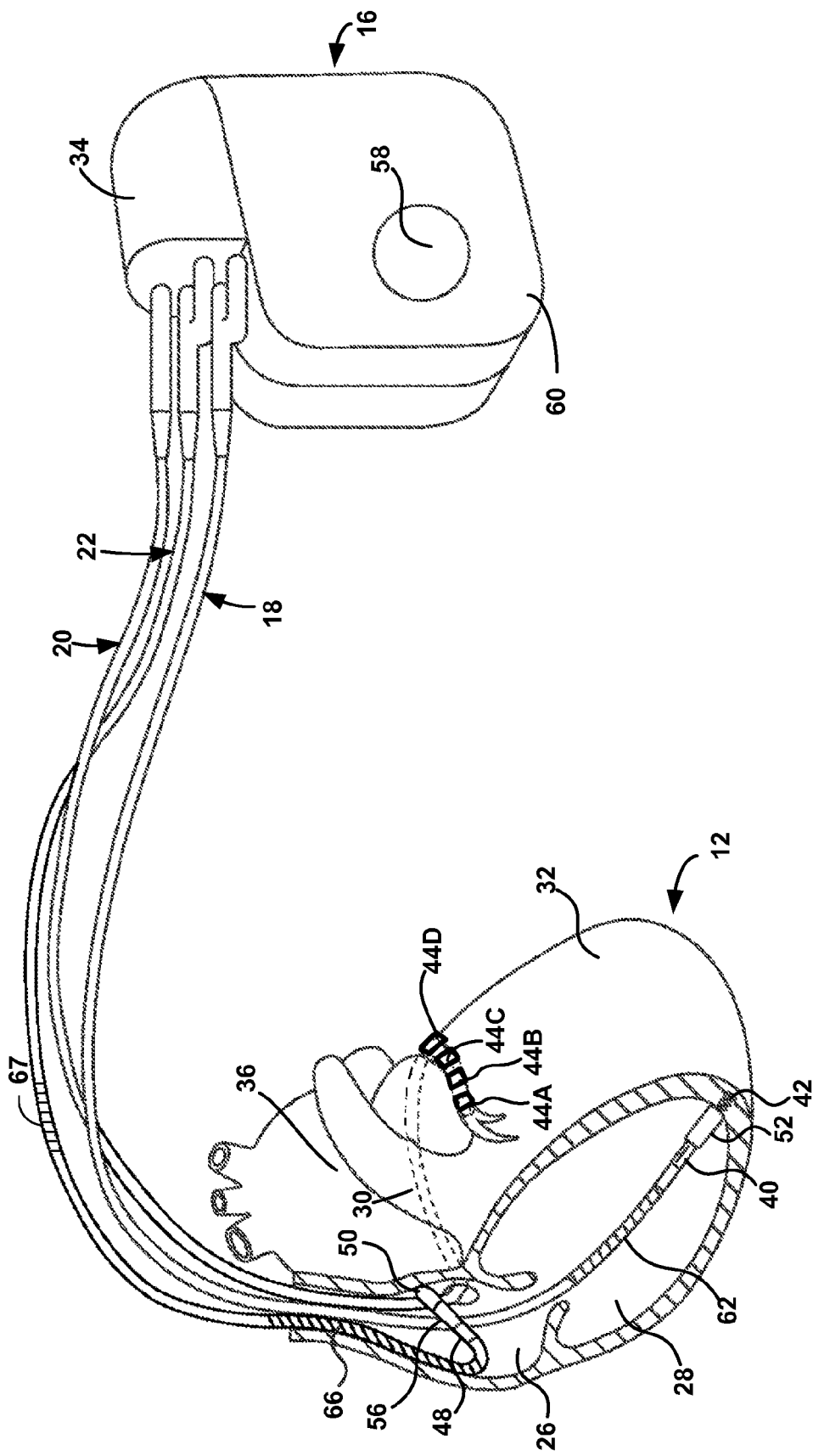
FIG. 2 is a conceptual diagram illustrating the example implantable medical device (IMD) and the leads of the system shown in FIG. 1 in greater detail.

FIG. 2 is a conceptual diagram illustrating IMD 16 and leads 18, 20, and 22 of therapy system 10 in greater detail. Leads 18, 20, 22 may be electrically coupled to a signal generator and a sensing module of IMD 16 via connector block 34.

Each of the leads 18, 20, 22 includes an elongated insulative lead body carrying one or more conductors. Bipolar electrodes 40 and 42 are located adjacent to a distal end of lead 18 and bipolar electrodes 48 and 50 are located adjacent to a distal end of lead 22. In some example configurations, lead 20 may be a quadripolar lead and, as such, include four electrodes, namely electrodes 44A-44D, which are located adjacent to a distal end of lead 20. Electrodes 40, 44A-44D, and 48 may take the form of ring electrodes, and electrodes 42 and 50 may take the form of extendable helix tip electrodes mounted retractably within insulative electrode heads 52 and 56, respectively.

Leads 18 and 22 also include elongated intracardiac electrodes 62 and 66 respectively, which may take the form of a coil. In addition, one of leads 18, 20, 22, e.g., lead 22 as seen in FIG. 2, may include a superior vena cava (SVC) coil 67 for delivery of electrical stimulation, e.g., transvenous defibrillation. For example, lead 22 may be inserted through the superior vena cava and SVC coil 67 may be placed, for example, at the right atrial/SVC junction (low SVC) or in the left subclavian vein (high SVC). Each of the electrodes 40, 42, 44A-44D, 48, 50, 62, 66 and 67 may be electrically coupled to a respective one of the conductors within the lead body of its associated lead 18, 20, 22, and thereby individually coupled to the signal generator and sensing module of IMD 16.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60.

IMD 16 may sense electrical signals attendant to the depolarization and repolarization of heart 12 via electrodes 40, 42, 44A-44D, 48, 50, 58, 62, 66 and 67. The electrical signals are conducted to IMD 16 via the respective leads 18, 20, 22, or in the case of housing electrode 58, a conductor coupled to the housing electrode. IMD 16 may sense such electrical signals via any bipolar combination of electrodes 40, 42, 44A-44D, 48, 50, 58, 62, 66 and 67. Furthermore, any of the electrodes 40, 42, 44A-44D, 48, 50, 58, 62, 66 and 67 may be used for unipolar sensing in combination with housing electrode 58.

In some examples, IMD 16 delivers pacing pulses via bipolar combinations of electrodes 40, 42, 44A-44D, 48 and 50 to produce depolarization of cardiac tissue of heart 12. In some examples, IMD 16 delivers pacing pulses via any of electrodes 40, 42, 44A-44D, 48 and 50 in combination with housing electrode 58 in a unipolar configuration. For example, electrodes 40, 42, and/or 58 may be used to deliver RV pacing to heart 12. Additionally or alternatively, electrodes 44A-44D and/or 58 may be used to deliver LV pacing to heart 12, and electrodes 48, 50 and/or 58 may be used to deliver RA pacing to heart 12.

Furthermore, IMD 16 may deliver defibrillation pulses to heart 12 via any combination of elongated electrodes 62, 66 and 67, and housing electrode 58. Electrodes 58, 62, and 66 may also be used to deliver cardioversion pulses to heart 12. Electrodes 62, 66 and 67 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIGS. 1 and 2. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36.

Two or more electrodes, and the polarity of the electrodes, define a vector, or path, for delivering pacing pulses to heart 12. As described above, there are numerous vectors that may be used to deliver pacing pulses to heart 12. For example, various combinations of the electrodes on a single quadripolar lead, i.e., a lead with four electrodes on the lead, such as lead 20, as well as combinations of the lead electrodes with an electrode on the housing of an IMD may provide sixteen different vectors that may be used to deliver pacing pulses to a chamber of heart 12 that the lead is within or on. Testing each vector in order to determine which vector at a particular voltage amplitude sufficiently captures the heart without unnecessarily depleting the battery, e.g., by pacing at too high a voltage, may be a time-consuming process.

Using the techniques of this disclosure, a clinician may quickly determine one or more electrode combinations of one or more leads of an implantable medical device that have an acceptable, e.g., relatively low, pacing threshold. As described in more detail below, in some cases, the pacing capture techniques may include measuring an atrioventricular (AV) interval of a patient and, for each of a plurality of vectors, delivering a pacing pulse at a voltage to a left ventricle of a heart, determining whether capture of the left ventricle occurred as a result of the pacing pulse, and iteratively adjusting the voltage and delivering pacing pulses at the adjusted voltages in order to determine a particular voltage at which capture or loss of capture (LOC) of the left ventricle occurs.

Figure 3:
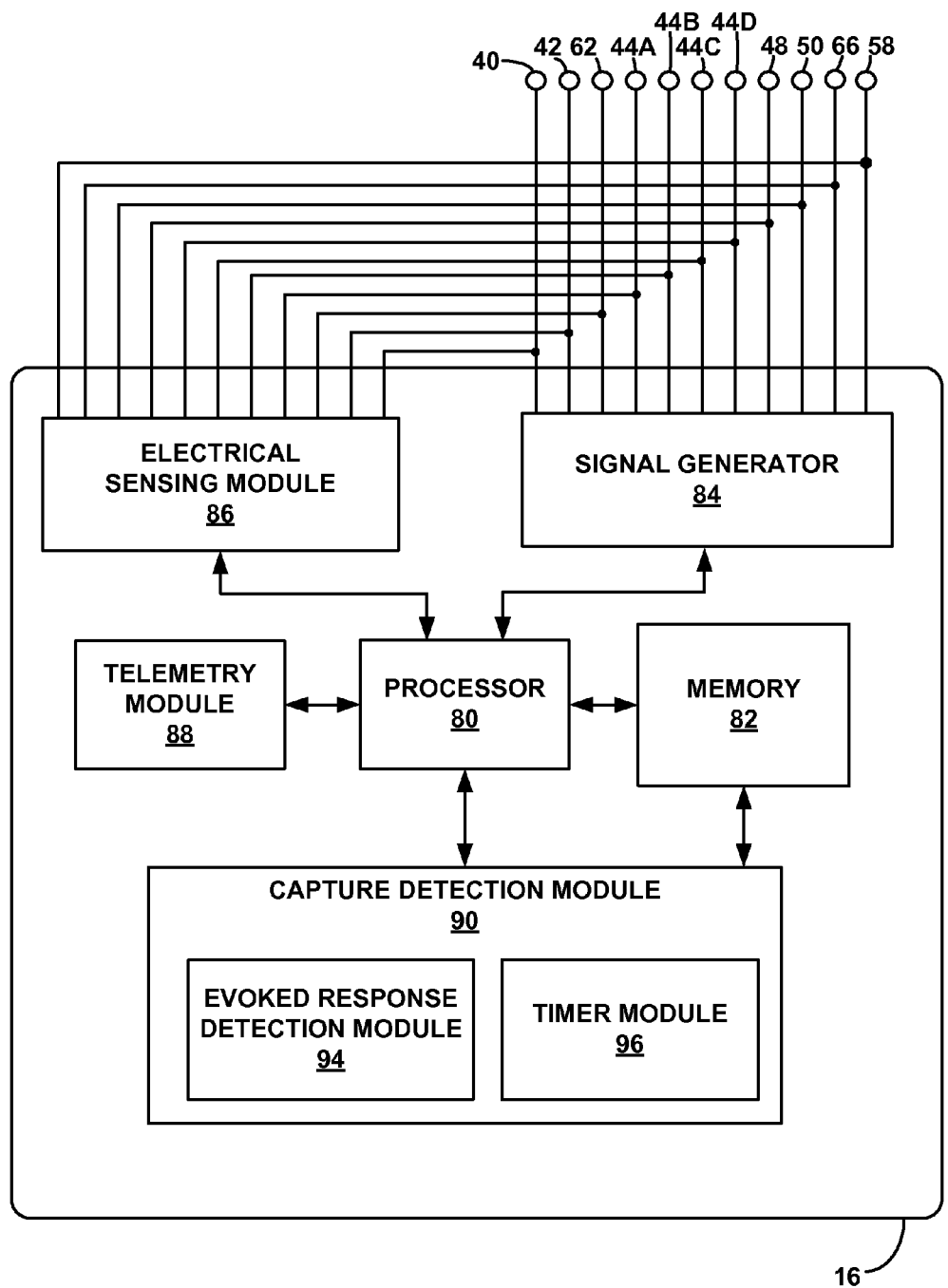
FIG. 3 is a block diagram illustrating an example configuration of an implantable medical device.

FIG. 3 is a block diagram illustrating one example configuration of IMD 16. In the example illustrated by FIG. 3, IMD 16 includes a processor 80, memory 82, signal generator 84, electrical sensing module 86, and telemetry module 88. IMD 16 further includes capture detection module 90, which itself includes evoked response detection module 94 and timer module 96. Memory 82 may include computer-readable instructions that, when executed by processor 80, cause IMD 16 and processor 80 to perform various functions attributed throughout this disclosure to IMD 16, processor 80, or capture detection module 90. The computer-readable instructions may be encoded within memory 82. Memory 82 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. In one example, capture detection module 90, evoked response detection module 94, and timer module 96 may be stored or encoded as instructions in memory 82 that are executed by processor 80.

Processor 80 controls signal generator 84 to deliver stimulation therapy, e.g., cardiac pacing or CRT, to heart 12 according to a selected one or more therapy programs, which may be stored in memory 82. Signal generator 84 is electrically coupled to electrodes 40, 42, 44A-44D, 48, 50, 58, 62, and 66, e.g., via conductors of the respective lead 18, 20, 22, or, in the case of housing electrode 58, via an electrical conductor disposed within housing 60 of IMD 16. Signal generator 84 is configured to generate and deliver electrical stimulation therapy to heart 12 via selected combinations of electrodes 40, 42, 44A-44D, 48, 50, 58, 62, and 66. In some examples, signal generator 84 is configured to delivery cardiac pacing pulses. In other examples, signal generator 84 may deliver pacing or other types of stimulation in the form of other signals, such as sine waves, square waves, or other substantially continuous time signals.

Stimulation generator 84 may include a switch module (not shown) and processor 80 may use the switch module to select, e.g., via a data/address bus, which of the available electrodes are used to deliver pacing pulses. Processor 80 may also control which of electrodes 40, 42, 44A-44D, 48, 50, 58, 62, and 66 is coupled to signal generator 84 for generating stimulus pulses, e.g., via the switch module. The switch module may include a switch array, switch matrix, multiplexer, or any other type of switching device suitable to selectively couple a signal to selected electrodes.

Electrical sensing module 86 monitors signals from at least one of electrodes 40, 42, 44A-44D, 48, 50, 58, 62, or 66 in order to monitor electrical activity of heart 12. Electrical sensing module 86 may also include a switch module to select which of the available electrodes are used to sense the cardiac activity. In some examples, processor 80 selects the electrodes that function as sense electrodes, or the sensing vector, via the switch module within electrical sensing module 86.

Electrical sensing module 86 includes multiple detection channels, each of which may be selectively coupled to respective combinations of electrodes 40, 42, 44A-44D, 48, 50, 58, 62, or 66 to detect electrical activity of a particular chamber of heart 12. Each detection channel may comprise an amplifier that outputs an indication to processor 80 in response to detection of an event, such as a depolarization, in the respective chamber of heart 12. In this manner, processor 80 may detect the occurrence of R-waves and P-waves in the various chambers of heart 12.

Memory 82 stores intervals, counters, or other data used by processor 80 to control the delivery of pacing pulses by signal generator 84. Such data may include intervals and counters used by processor 80 to control the delivery pacing pulses to one or both of the left and right ventricles for CRT. The intervals and/or counters are, in some examples, used by processor 80 to control the timing of delivery of pacing pulses relative to an intrinsic or paced event, e.g., in another chamber.

In one example, capture detection module 90 uses signals from electrical sensing module 86 to detect capture and/or inadequate capture when signal generator 84 delivers a pacing pulse. Via the switching module, processor 80 may control which of electrodes 40, 42, 44A-44D, 48, 50, 58, 62, and 66 is coupled to electrical sensing module 86 to detect a depolarization in a second chamber, e.g., the RV, subsequent to the delivery of a pacing pulse to a first chamber, e.g., the LV, for the determination of whether the pacing pulse captured the first chamber. Processor 80 may also control which of electrodes 40, 42, 44A-44D, 48, 50, 58, 62, and 66 is coupled to electrical sensing module 86 to detect an evoked electrical response in the first chamber to the pacing pulse in the first chamber. Memory 82 may store predetermined intervals or voltage thresholds which define whether a detected signal has an adequate magnitude and is appropriately timed relative to the pacing pulse to be considered a depolarization in the second chamber indicative of capture or an evoked response in the first chamber. In some examples, a channel of electrical sensing module 86 used to detect capture comprises an amplifier which provides an indication to processor 80 when a detected signal has an adequate magnitude.

Processor 80 controls the selection of electrode configurations for delivering pacing pulses and for detecting capture and/or loss of capture. Processor 80, for example, may communicate with signal generator 84 to select two or more stimulation electrodes in order to generate one or more pacing pulses for delivery to a selected chamber of heart 12. Processor 80 may also communicate with electrical sensing module 86 to select two or more sensing electrodes for capture detection based on the chamber to which the pacing pulse is delivered by signal generator 84.

Capture detection module 90, in the example of FIG. 3, is capable of detecting capture and LOC during capture detection tests. Capture detection module 90 uses timer module 96 to determine when to deliver pacing pulses and to determine conduction times between chambers of the heart. In addition, as seen in FIG. 3, capture detection module 90 further includes evoked response detection module 94 for detecting the amplitude and timing of an evoked response.

Using certain techniques of this disclosure, capture detection module 90 may determine pacing capture thresholds for each of a plurality of pacing vectors by, for each of the vectors, delivering pacing pulses at various voltage levels, determining left ventricle pace (LVP) to right ventricle sense (RVS) conduction times in response to each of the pacing pulses, and determining a voltage at which capture/loss-of-capture (LOC) occurs. Briefly, the pacing capture test techniques of this disclosure may include pacing an atrium, measuring an intrinsic atrioventricular (AV) interval of a patient in response to the delivered pace, delivering a pacing pulse at a voltage to the left ventricle of the heart, determining whether capture occurred as a result of the pacing pulse, and iteratively adjusting the voltage and delivering pacing pulses at the adjusted voltages in order to determine a particular voltage at which capture or LOC occurs.

Before delivering any pacing pulses, a basic stability test is performed on a patient. The basic stability test monitors the patient's current heart rhythm in order to verify the stability and rate of the patient's heart. For example, the stability test may monitor the intrinsic ventricular rate of the patient's heart. If the rate is too high or the heart is unstable, the pacing capture test aborts. If the rate and stability are considered acceptable, however, then the pacing capture test may continue. The amplitude of the pacing pulse, the pacing configuration, and the vector may be recorded and used later as a "normal" configuration for any backup pacing cycles delivered throughout the pacing capture test. A pacing configuration may include programmable pacing settings, such as whether pacing is set to be RV only, RV to LV, LV to RV, or LV only, as well as the rate, amplitude, and other settings that may be altered for the "test" pulses.

In accordance with certain techniques of this disclosure, an AV measurement cycle is performed after the successful completion of the basic stability test. A pacing cycle is created that allows the time from the atrial depolarization to the right ventricular depolarization to be measured. One possible method of measuring the intrinsic AV interval is described below. In particular, processor 80 controls signal generator 84 to deliver a pacing pulse to the right atria (RA). At a predetermined time after the pacing pulse to the RA is delivered, e.g., about 0 milliseconds (ms) to about 60 ms following the RA pacing pulse, timer module 96 and processor 80 control signal generator 84 to deliver a pacing pulse with an amplitude of zero volts (V) to the LV. This zero volt pacing pulse to the LV ensures that there will be no capture. Electrical sensing module 86 and capture detection module 90 sense for RV depolarization. The RV depolarization detected by capture detection module 90 must have been generated by the right atria (A). The time between the right atrial pace and the RVS, and/or the time between the zero-volt LVP and the RVS, is recorded and used later in the test to determine whether a non-zero LV pacing pulse resulted in capture, as described in more detail below. It should be noted that the zero-volt pace is only one possible way to determine an AV measurement cycle.

Again, in the AV measurement cycle, no pacing pulses are delivered to either ventricle. Rather, the right atria may be paced. As will become apparent below, IMD 16 delivers a zero volt pacing pulse to the left ventricle so that later in the pacing capture test, the timing of delivery of LV pacing pulses is based off of a common reference point for ease of comparison of conduction times. The AV measurement cycle is used to determine the A-RVS conduction time. Later, as described below, processor 80 controls signal generator 84 to deliver LV-only paces (LVP) and electrical sensing module 86 and capture detection module 90 measure LVP-RVS conduction times. For capture to have occurred as a result of the LV-only pace, the LVP-RVS time must be shorter than the A-RVS minus the A to LVP (or zero-volt LVP-RVS) time determined during the AV measurement cycle.

Following the basic stability test and AV measurement cycle, processor 80 controls signal generator 84 to overdrive the patient's heart rate, e.g., by using shorter A-A and/or A-V intervals in order to lower the chances of competing atrial or ventricular depolarizations. The remainder of the pacing capture threshold test is performed at this overdriven rate. Throughout the remainder of the pacing capture threshold test, it may be desirable to periodically deliver one or more backup or safety cycles, delivered at the overdriven rate using the "normal" configuration used above in the basic stability test, in order to guarantee delivery of a pacing pulse which will capture.

The pacing capture threshold test of this disclosure delivers pacing pulses within a range of voltages, e.g., about 6V to about 0V. In one example implementation, capture detection module 90 selects an initial voltage to be delivered to the left ventricle of the patient's heart that is approximately in the middle of the range of voltages, e.g., about 3V. Capture detection module 90 selects a vector among the plurality of vectors to be tested and processor 80 controls signal generator 84 to pace the RA and, at a predetermined time after the pacing pulse to the RA is delivered, e.g., about 0 ms to about 60 ms following the RA pacing pulse, timer module 96 and processor 80 control signal generator 84 to deliver a LV-only pacing pulse (LVP) via the selected vector.

After the pacing pulse is delivered, electrical sensing module 86 and capture detection module 90 determine whether there is evidence of capture. In accordance with certain techniques of this disclosure, electrical sensing module 86 and capture detection module 90 determine the time at which a corresponding depolarization on the right side of the heart occurs (RVS) and, based on this time, determine whether capture has occurred. In particular, capture detection module 90 compares the A-RVS time (or zero-volt LVP-RVS time) determined above during the AV measurement cycle to the measured LVP-RVS conduction time. In order for capture to have occurred, the measured LVP-RVS conduction time, plus the predetermined time between the RA pace and the LVP, should be less than the A-RVS time (or zero-volt LVP-RVS time) determined during the AV measurement cycle, as depicted and described below with respect to FIGS. 4A-4C. In one example, capture detection module 90 module may utilize a threshold interval based on the A-RVS time less a margin, e.g., 30-40 ms, in order to determine if capture occurred, as described in more detail below. In some example implementations, if an ectopic event inhibits the test pacing cycle, e.g., a premature ventricular contraction (PVC), then an additional attempt at the test pacing cycle may be attempted, e.g., per voltage amplitude, per vector.

Figure 4A:
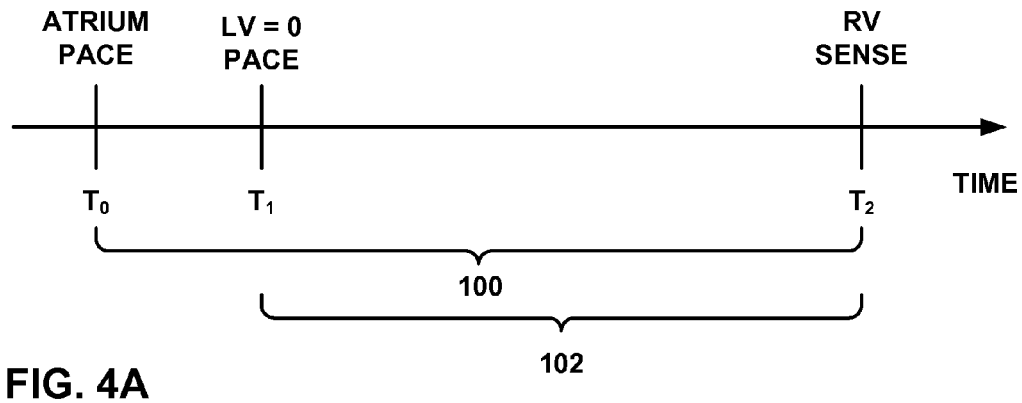
FIGS. 4A-4C are conceptual timing diagrams illustrating techniques for determining an inter-chamber pace to sense interval.
Figure 4B:
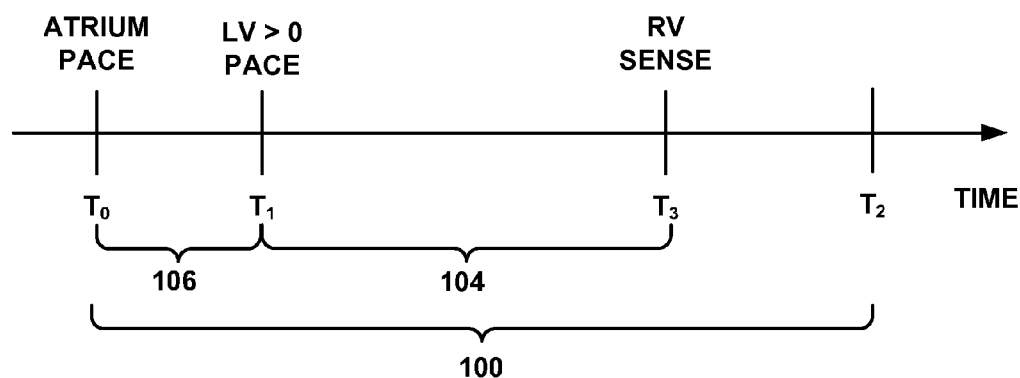
Figure 4C:
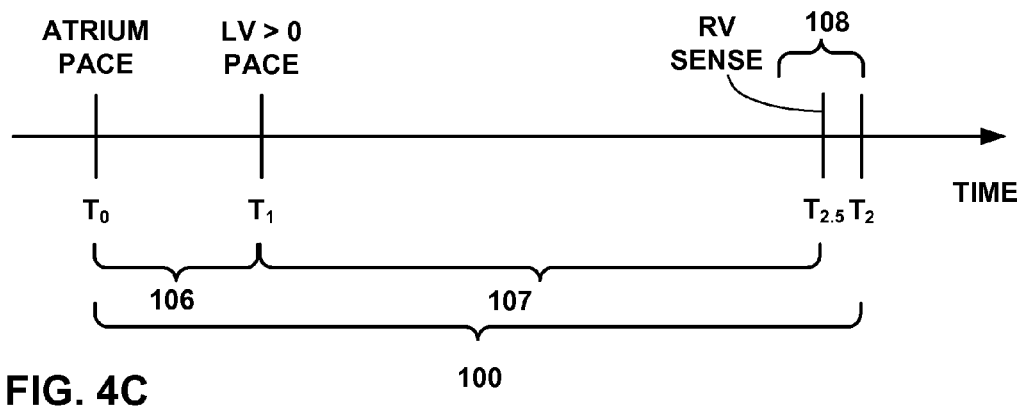

FIGS. 4A-4C are conceptual timing diagrams illustrating techniques for determining an inter-chamber pace to sense interval. FIG. 4A depicts a simplified A-RVS timing diagram determined during the AV measurement cycle described above. In FIG. 4A, the right atrium is paced at time $T_0$. A predetermined time later, at time $T_1$, the left ventricle is paced with a 0V pacing pulse. Finally, the right ventricle is sensed at time $T_2$. The A-RVS time $T_2-T_0$, shown at 100, is the time between atrial depolarization and the right ventricular depolarization and serves as the baseline for determining whether a non-zero pacing pulse captures. The LVP (zero volt)-RVS time $T_2-T_1$, shown at 102, is the time between the left ventricle 0V pacing pulse and the right ventricular depolarization and serves as an alternate baseline for determining whether a non-zero pacing pulse captures.

FIG. 4B depicts a simplified LVP-RVS conduction time timing diagram for a non-zero pacing pulse delivered to the left ventricle. In FIG. 4B, the right atrium is paced at time $T_0$. A predetermined time later, at time $T_1$, the left ventricle is paced with a non-zero pacing pulse. Finally, the right ventricle is sensed at time $T_3$. In order to determine whether the pacing pulse, i.e., LVP, captured, the time between the left ventricle pacing pulse, $T_1$, and the RV sense, $T_3$, shown at 104, plus the predetermined time between the right atrium pace and the LVP, shown at 106, must be less than the A-RVS time, shown at 100 and above in FIG. 4A, determined during the AV measurement cycle. In other words, time $T_3-T_0$ in FIG. 4B, shown as 104, 106, must be less than the A-RVS time $(T_2-T_0)$ in FIG. 4B, shown as 100, in order for capture to have occurred. Alternatively, in order to determine whether the pacing pulse, i.e., LVP, captured, the time between the left ventricle pacing pulse, T1, and the RV sense, T3, shown at 104, must be less than the LVP (zero volt)-RVS time $T_2-T_1$, shown at 102 in FIG. 4A, determined during the AV measurement cycle.

FIG. 4C depicts a simplified LVP-RVS conduction time timing diagram for a non-zero pacing pulse delivered to the left ventricle where capture does not occur. In FIG. 4C, the right atrium is paced at time $T_0$. A predetermined time later, at time $T_1$, the left ventricle is paced with a non-zero pacing pulse. Finally, the right ventricle is sensed at time $T_3$. In order to determine whether the pacing pulse, i.e., LVP, captured, the time between the left ventricle pacing pulse, $T_1$, and the RV sense, $T_3$, shown at 104, plus the predetermined time between the right atrium pace and the LVP, shown at 106, must be less than the A-RVS time, shown at 100, determined during the AV measurement cycle. In other words, time $T_3-T_0$ in FIG. 4B, shown as 102, 104, must be less than the A-RVS time ($T_2-T_0$), shown as 100, in order for capture to have occurred.

In the example depicted in FIG. 4C, the time between the left ventricle pacing pulse, $T_1$, and a first RV sense, $T_{2.5}$, shown at 107, plus the predetermined time between the right atrium pace and the LVP, shown at 106, is slightly less than the A-RVS time, shown at 100, determined during the AV measurement cycle. Nevertheless, capture may not have occurred. In one example aspect of the techniques of this disclosure, a threshold time interval may be set, e.g., by a user, such that in order for capture detection module 90 to determine that capture occurred, the RV sense must be outside of that threshold time interval. For example, in FIG. 4C, capture detection module 90 may utilize a settable threshold time interval 108 based on the A-RVS time less a margin, e.g., about 30 ms to about 40 ms, to determine whether capture occurred. If capture detection module 90 determines that the RV sense occurred within a non-capture window, shown as threshold time interval 108, capture detection module 90 determines loss of capture. For example, in FIG. 4C, the first RV sense occurred at time $T_{2.5}$. However, RV sense time $T_{2.5}$ is within the non-capture window, shown as threshold time interval 108 and, as such, it is difficult to determine whether capture occurred. Thus, capture detection module 90 determines loss of capture for that pacing pulse.

To summarize, capture detection module 90 determines loss of capture if either of the following scenarios occurs: 1) if the first RV sense after the LV-only pace occurs at or after the RV sense time $T_2$ determined during the AV measurement cycle described above with respect to FIG. 4A, or 2) if the first RV sense after the LV-only pace is prior to the RV sense time $T_2$ determined during the AV measurement cycle described above with respect to FIG. 4A, but within a non-capture window, shown as threshold time interval 108 in FIG. 4C. Capture detection module 90 determines that capture occurred if the first RV sense after the LV-only pace is prior to time $T_2$ determined during the AV measurement cycle described above with respect to FIG. 4A and not within non-capture window, shown as threshold time interval 108 in FIG. 4C, and if the RV sense is determined to be a physiological sense.

It should be noted that if there was no RVS, or there was an extremely long A-RVS time in the AV test, then a default maximum value might be used to set the start of the non-capture window. The non-capture window may be a set amount of time before the RV sense time $T_2$ determined during the AV measurement cycle described above with respect to FIG. 4A.

Referring again to FIG. 3, if there is evidence that the pacing pulse captured, e.g., as determined by the LVP-RVS conduction times and/or by detection of an evoked response in the LV, then capture detection module 90 selects another voltage at which to deliver a pacing pulse, using the same vector, to the left ventricle of the patient's heart that is less than the initial voltage. Capture detection module 90 also selects a minimum voltage within the range of voltages below which pacing pulses will not be delivered. For example, capture detection module 90 may select a voltage of about 2V at which to deliver the next pacing pulse and select a minimum voltage of 0V. Using the previously selected vector, processor 80 controls signal generator 84 to pace the RA and, at a predetermined time after the pacing pulse to the RA is delivered, timer module 96 and processor 80 control signal generator 84 to deliver a LV-only pacing pulse (LVP) via the selected vector. Again, the pacing capture threshold test is attempting to determine the minimum voltage that will capture, which will reduce power consumption and extend battery life.

If there is evidence that the pacing pulse captured, then capture detection module 90 selects another voltage at which to deliver a pacing pulse, using the same vector, to the left ventricle of the patient's heart that is less than the previous voltage. For example, capture detection module 90 may select a voltage of about 1V at which to deliver the next pacing pulse. Using the previously selected vector, processor 80 controls signal generator 84 to pace the RA and, at a predetermined time after the pacing pulse to the RA is delivered, timer module 96 and processor 80 control signal generator 84 to deliver a LV-only pacing pulse (LVP) via the selected vector.

This process of iteratively decreasing the voltage of the pacing pulse and another pacing pulse to the left ventricle at the decreased voltage within the range of voltages continues until depolarization does not occur in the right ventricle within the time interval, i.e., the LVP-RVS conduction time plus the predetermined time following deliver of the RA pace should be less than the A-RVS time measured during the AV measurement cycle, or until the minimum voltage, e.g., 0V, is reached. If depolarization does not occur, i.e., there is no RVS corresponding to the LVP, then processor 80 writes the capture/LOC voltages for the selected vector, as determined by capture detection module 90, to memory 82. For example, assuming that capture occurred at 2V, but capture did not occur at 1V, processor 80 may store 2V as the capture voltage for the selected vector in memory 82.

This completes the test of the originally selected vector, assuming that there was evidence of capture at the initially selected voltage, e.g., 3V. If, however, there was no evidence of capture at the initially selected voltage, then the test assumes that lowering the voltage of pacing pulses also will not capture. As such, if there was no evidence of capture at the initially selected voltage, then the pacing capture threshold test of this disclosure increases the voltage to the maximum value of the range of voltages, e.g., 6V, and through a range of voltages between the maximum voltage and the initial voltage, iteratively decreases the maximum voltage and delivers pacing pulses to the left ventricle until depolarization occurs in the right ventricle within the time interval i.e., the LVP-RVS conduction time plus the predetermined time following deliver of the RA pace should be less than the A-RVS time measured during the AV measurement cycle, or until the initial voltage plus one step of resolution, e.g., 3V plus 1V (or 0.5V, 0.25V, etc.), is reached.

It should be noted that the iterative technique described above is only one possible search method for determining a capture threshold. In other examples, processor 80 may control signal generator 84 to iteratively increase the voltage if the initial voltage does not capture. In another example, processor 80 may control signal generator 84 to begin at a voltage that captured most recently and increase or decrease the voltage from that voltage.

Using the techniques of this disclosure and assuming that there was no evidence of capture at the initially selected voltage, e.g., 3V, capture detection module 90 selects a maximum voltage to be delivered to the left ventricle of the patient's heart, e.g., about 6V. Processor 80, using the initially selected vector, controls signal generator 84 to pace the RA and, at a predetermined time after the pacing pulse to the RA is delivered, e.g., about 5 ms to about 40 ms following the RA pacing pulse, timer module 96 and processor 80 control signal generator 84 to deliver a LV-only pacing pulse (LVP) via the selected vector.

After the pacing pulse is delivered, electrical sensing module 86 and capture detection module 90 determine whether there is evidence of capture. In one example, in accordance certain techniques of this disclosure, electrical sensing module 86 and capture detection module 90 determine the time at which a corresponding depolarization on the right side of the heart occurs (RVS) and, based on this time, determine whether capture has occurred. In particular, capture detection module 90 compares the A-RVS time determined above during the AV measurement cycle to the measured LVP-RVS conduction time. Again, in order for capture to have occurred, the measured LVP-RVS conduction time, plus the predetermined time that followed the RA pace and preceded the LVP, should be less than the A-RVS time determined during the AV measurement cycle.

If there is evidence that the pacing pulse captured, e.g., as determined by the LVP-RVS conduction times and/or by detection of an evoked response, then capture detection module 90 selects another voltage at which to deliver a pacing pulse, using the same vector, to the left ventricle of the patient's heart that is less than the maximum voltage. Capture detection module 90 also selects a stop voltage within the range of voltages below which pacing pulses will not be delivered. For example, capture detection module 90 may select a voltage of about 5V at which to deliver the next pacing pulse and select a stop voltage that is greater than the initially tested voltage of 3V, e.g., about 4V. Using the previously selected vector, processor 80 controls signal generator 84 to pace the RA and, at a predetermined time after the pacing pulse to the RA is delivered, timer module 96 and processor 80 control signal generator 84 to deliver a LV-only pacing pulse (LVP) via the selected vector. Again, the pacing capture threshold test is attempting to determine the minimum voltage that will capture, which will reduce power consumption and extend battery life.

If there is evidence that the pacing pulse captured, then capture detection module 90 selects another voltage at which to deliver a pacing pulse, using the same vector, to the left ventricle of the patient's heart that is less than the previous voltage. For example, capture detection module 90 may select a voltage of about 4V at which to deliver the next pacing pulse. Using the previously selected vector, processor 80 controls signal generator 84 to pace the RA and, at a predetermined time after the pacing pulse to the RA is delivered, timer module 96 and processor 80 control signal generator 84 to deliver a LV-only pacing pulse (LVP) via the selected vector.

If depolarization does not occur, i.e., there is no RVS corresponding to the LVP, then processor 80 writes the capture/LOC voltages for the selected vector, as determined by capture detection module 90, to memory 82. For example, assuming that capture occurred at 4V, processor 80 may store 4V as the capture voltage for the selected vector in memory 82.

This completes the test of the originally selected vector. Capture detection module 90 then selects another vector to be tested. In a manner similar to that described above, capture detection module 90 selects an initial voltage to be delivered to the left ventricle of the patient's heart that is approximately in the middle of the range of voltages, e.g., about 3V. Processor 80 then controls signal generator 84 to pace the RA and, at a predetermined time after the pacing pulse to the RA is delivered, timer module 96 and processor 80 control signal generator 84 to deliver a LV-only pacing pulse (LVP) via the selected vector. If there is evidence of capture, capture detection module 90 iteratively decrements the voltage of the pacing pulses toward a minimum voltage and delivers pacing pulses via the selected vector until there is no evidence of capture. If, however, there is no evidence of capture using the pacing pulse delivered at the initial voltage, capture detection module 90 increases the voltage of the pacing pulse to a maximum voltage, which presumably will capture, and iteratively decrements the voltage of the pacing pulses toward the initial voltage and delivers pacing pulses via the selected vector until there is no evidence of capture or until the initial voltage (which has already shown no evidence of capture) is reached.

It should be noted that although the voltages described above iteratively decreased by steps of 1V during the test, i.e., steps having a resolution of 1V, the techniques of this disclosure are not so limited. Rather, the resolution may be 0.5V, 0.25V, 0.125V, or some other resolution. In addition, the resolution need not be the same throughout the test. Rather, higher voltages may have lower resolutions than lower voltages. For example, for pacing pulses at or below 3V, the test may decrement voltages by steps of 0.5V or less, while for pacing pulses between 6V and 3V, the test may decrement voltages by 1V. In some example implementations, these resolutions may be programmable, e.g., by a clinician.

In another example implementation, electrical sensing module 86 and capture detection module 90 determine whether capture has occurred based on the LVP-RVS conduction times, as described above, as well as the evoked response in the LV. In particular, electrical sensing module 86 and evoked response detection module 94 of capture detection module 90 determine whether there has been an evoked response by measuring the amplitude of the response in the LV as well as time between the LVP and the evoked response in the LV. In order for capture to have occurred, the time between the LVP and the evoked response in the LV should be within a prescribed window, and the amplitude of the response should be greater than some threshold value. Processor 80 may retrieve the previously stored threshold value from memory 82 and capture detection module 90 may compare the measured amplitude of the response to the threshold value. In addition, for each vector tested at each particular voltage, processor 80 may store the measured LV response amplitude along with the time between the LVP and the evoked response in the LV as data in memory 82. In such an example implementation, the pacing capture threshold test may conclude that capture has occurred for a tested vector at a particular voltage if the following occur: the LVP-RVS conduction time is less than the A-RVS time and the time between the LVP and the evoked response in the LV is within the prescribed evoked response window; and the amplitude of the response in the LV is above the threshold value.

Capture detection module 90 may output to a clinician a list of vectors and the capture or loss of capture voltages associated with each vector. In this manner, the pacing capture test techniques of this disclosure may quickly and accurately measure the estimated tissue pacing capture thresholds for one or more pacing vector configurations, thereby allowing a clinician to select particular vectors for the implantable medical device (IMD) that will deliver sufficient energy to pace the heart without unnecessarily depleting the battery.

In some examples, capture detection module 90 may rank or order the tested vectors, e.g., in order of increasing voltage amplitude. The clinician may specify the order in which the vectors should be listed, e.g., high voltage to low voltage, low voltage to high voltage. In addition, capture detection module 90 may sort the tested vectors according to characteristics, e.g., impedance and voltage, provided by the clinician, for example. In some examples, capture detection module 90 may automatically select tested vectors based on previously defined criteria.

Figure 8:
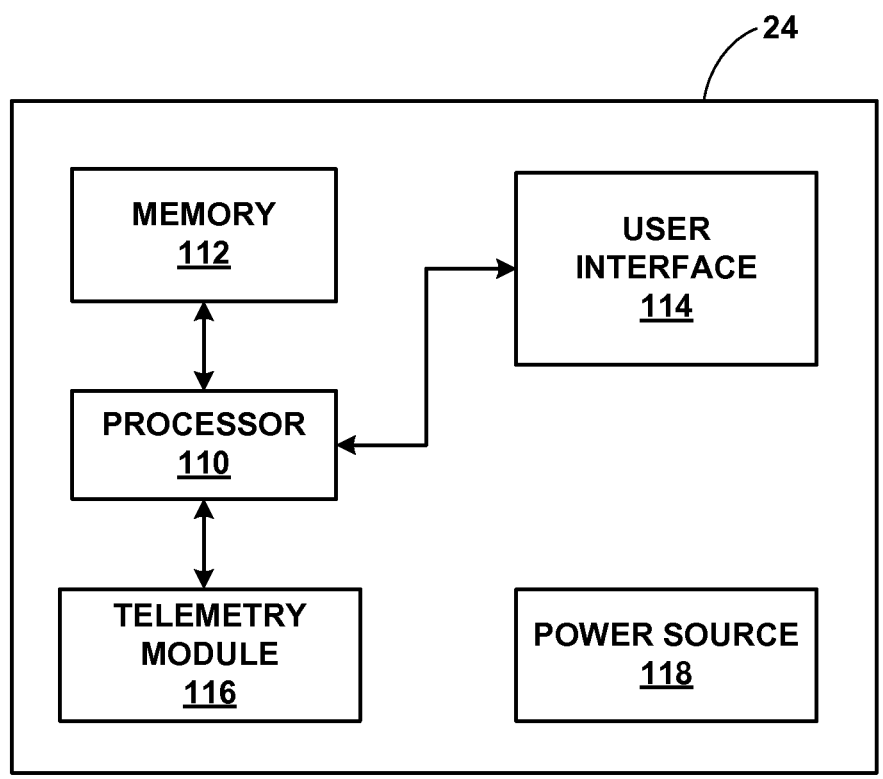
FIG. 8 is a functional block diagram illustrating an example configuration of the programmer of FIG. 1.

In one example implementation, a processor may control a user interface, e.g., user interface 114 of programmer 24 of FIG. 8, to provide a "check box" or some other graphic which may receive input from a user. Using the check box, a clinician may provide input to programmer 24 if undesired muscle and/or nerve stimulation occurred for a particular vector. In other words, the clinician may tag a vector if undesirable muscle and/or nerve stimulation occurred. Providing input in this manner may be allow tagged vectors to be ranked lower than untagged vectors. Tagged vectors may be communicated back to the IMD, e.g., via telemetry module 116 of programmer 24 of FIG. 8, so that the IMD would be able to provided that information to other programmers at later dates, thereby allowing the clinicians the option to exclude vectors with a history of undesired stimulation in future test runs.

In other example implementations, the clinician may specify that only some of the available vectors should be tested. For example, for a quadripolar lead, although there are sixteen possible vectors, a clinician may only be interested in the ten most commonly used vectors, or some other subset of the total available vectors. As such, the clinician may specify, e.g., using programmer 24, the particular vectors that should be tested for pacing capture thresholds. In some examples, clinicians may save their preferred vectors for a given lead, and then load and run a test using those preferred vectors.

In another example implementation, processor 80 and electrical sensing module 86 may perform impedance measurements for each vector during the pacing capture threshold tests. Processor 80 may control electrical sensing module 86 to perform the impedance measurements tests in parallel with the pacing capture threshold tests. These impedance values may be displayed along with the pacing capture threshold values to the clinician, e.g., via programmer 24, at the end of test.

In one example implementation, a clinician may specify that only vectors having certain qualities, e.g., certain voltages and impedances, should be displayed upon completion of the pacing capture threshold test. For example, a clinician may specify, e.g., using programmer 24, that only vectors having capture thresholds that are less than about 3V and having impedances of less than about 10 ohms should be displayed.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide data to be uplinked to programmer 24 and receive data from programmer 24 via telemetry module 88.

Figure 5:
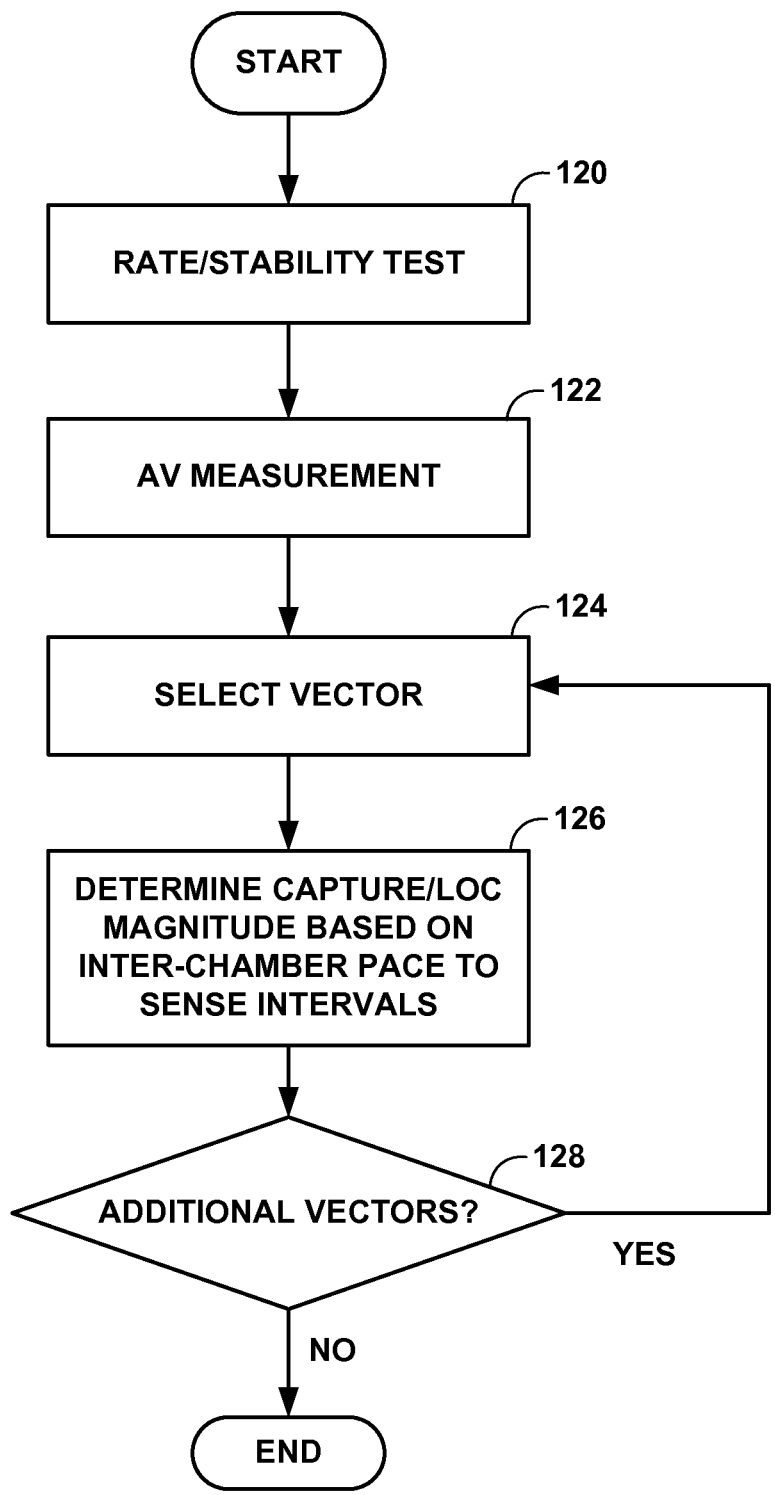
FIG. 5 is a flow diagram illustrating an example method for determining pacing capture thresholds in accordance with this disclosure.

FIG. 5 is a flow diagram illustrating an example method for determining pacing capture thresholds in accordance with this disclosure. As shown in FIG. 5, capture detection module 90 (FIG. 3) performs a basic rate or stability test on a patient before delivering any pacing pulses (120). After the successful completion of the basic stability test, capture detection module 90 performs an AV measurement cycle (122). A pacing cycle is created that allows the time from the atrial depolarization to the right ventricular depolarization to be measured. In particular, processor 80 (FIG. 3) controls signal generator 84 (FIG. 3) to deliver a pacing pulse to the right atria (RA). At a predetermined time after the pacing pulse to the RA is delivered, e.g., about 0 milliseconds (ms) to about 60 ms following the RA pacing pulse, timer module 96 (FIG. 3) and processor 80 (FIG. 3) control signal generator 84 (FIG. 3) to deliver a pacing pulse with an amplitude of zero volts (V) to the LV. This zero volt pacing pulse to the LV ensures that there will be no capture. Electrical sensing module 86 (FIG. 3) and capture detection module 90 (FIG. 3) sense for RV depolarization and/or the evoked response detector searches for LV evoked response. The RV depolarization detected by capture detection module 90 (FIG. 3) must have been generated by the right atria (A). The time between the right atrial pace and the RVS, and/or the time between the zero-volt LVP and the RVS, and/or the LV evoked response information is recorded and used later in the test to determine whether a non-zero LV pacing pulse resulted in capture.

Following the basic stability test and AV measurement cycle, processor 80 controls signal generator 84 to overdrive the patient's heart rate and capture detection module 90 selects a vector to test (124). Capture detection module 90 then determines capture or loss of capture magnitude for the vector based on the inter-chamber pace-to-sense intervals (126). In order for capture to have occurred, the measured LVP-RVS conduction time, plus the predetermined time between the RA pace and the LVP, should be less than the A-RVS time (or zero-volt LVP-RVS time) determined during the AV measurement cycle. If additional vectors are to be tested, capture detection module 90 selects another vector to test ("YES" branch of 128), otherwise the test ends ("NO" branch of 128).

Figure 6:
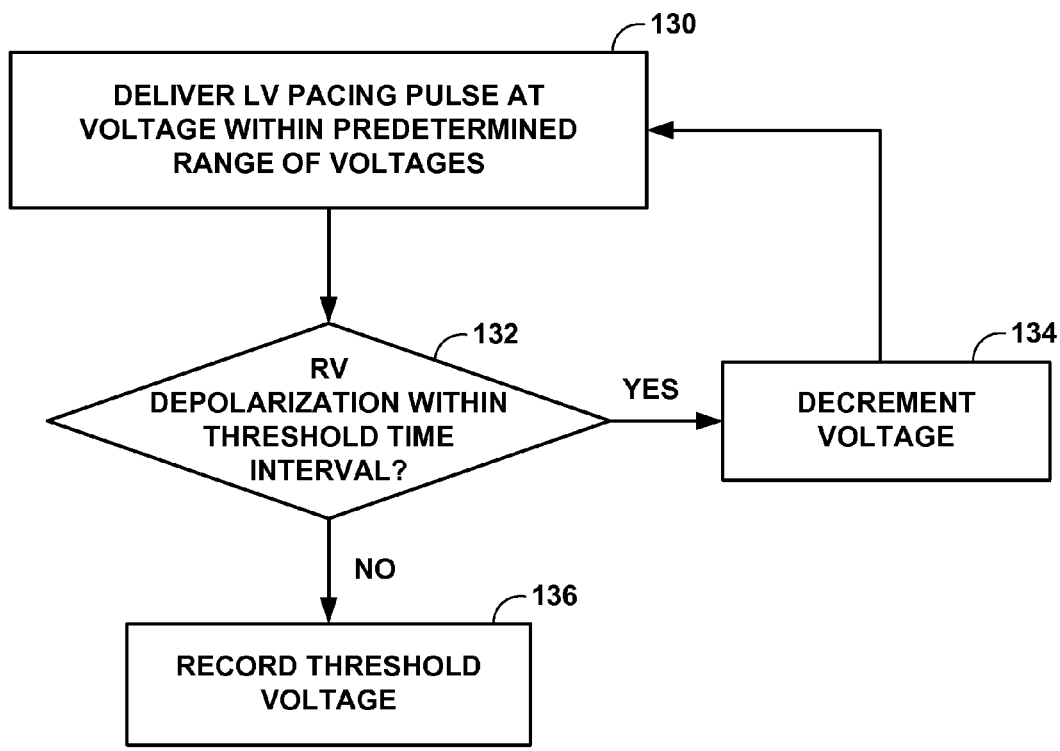
FIG. 6 is a flow diagram illustrating an example method for determining pacing capture thresholds in accordance with this disclosure.

FIG. 6 is a flow diagram illustrating another example method for determining pacing capture thresholds in accordance with this disclosure. In the flow diagram depicted of FIG. 6, processor 80 (FIG. 3) controls signal generator 84 (FIG. 3) to deliver a first pacing pulse, e.g., LV pacing pulse only, having a first voltage within a predetermined range of voltages to a ventricle of a heart (130). For example, the first pacing pulse may be approximately within the middle of a predetermined range of voltages. By way of specific example, the first pacing pulse may be about 3V and the predetermined range of voltages may be between about 6V and about 0.1V.

After the first pacing pulse is delivered to the left ventricle, electrical sensing module 86 (FIG. 3) and capture detection module 90 (FIG. 3) determine if depolarization occurred in the right ventricle of the heart within a time interval that is less than an intrinsic AV interval (132). That is, electrical sensing module 86 and capture detection module 90 determine the time at which a corresponding depolarization on the right side of the heart occurs (RVS) and, based on this time, determine whether capture has occurred. In particular, capture detection module 90 compares the A-RVS time determined above during the AV measurement cycle to the measured LVP-RVS conduction time. In order for capture to have occurred, the measured LVP-RVS conduction time, plus the predetermined time between the RA pace and the LVP, should be less than the A-RVS time determined during the AV measurement cycle, as depicted and described above with respect to FIGS. 4A-4C. In some example implementations, if an ectopic event inhibits the test pacing cycle, e.g., a premature ventricular contraction (PVC), then an additional attempt at the test pacing cycle may be attempted, e.g., per voltage amplitude, per vector.

If electrical sensing module 86 (FIG. 3) and capture detection module 90 (FIG. 3) determine that depolarization occurred, then processor 80 (FIG. 3) controls signal generator 84 (FIG. 3) to iteratively decrease the first voltage, e.g., about 3V, and deliver a second pacing pulse to the left ventricle at a decreased voltage, e.g., about 2.5V, within the range of voltages, e.g., about 6V to about 0.1V, until depolarization does not occur in the right ventricle within the time interval (134).

For example, one or more additional pacing pulse(s) of about 2.5V may be delivered and, if depolarization occurs, additional pacing pulse(s) of about 2V may be delivered. If depolarization occurs, additional pacing pulse(s) of about 1.5V may be delivered. If depolarization did not occur at the pacing pulse(s) of 2V, then loss of capture is declared and a threshold is recorded (136).

Figure 7:
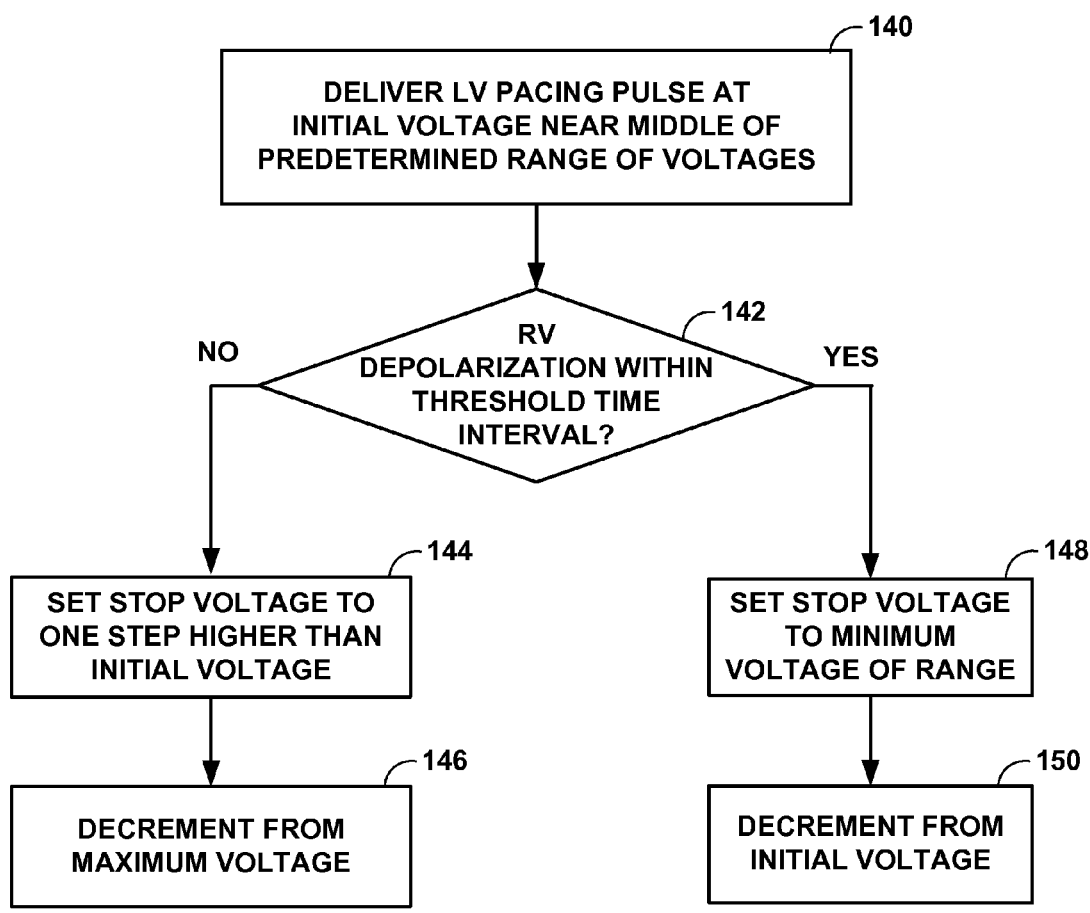
FIG. 7 is a flow diagram illustrating the example method of FIG. 6 for determining pacing capture thresholds in more detail.

FIG. 7 is a flow diagram illustrating the example method of FIG. 6 for determining pacing capture thresholds in more detail. Capture detection module 90 selects an initial voltage to be delivered to the left ventricle of the patient's heart that is approximately in the middle of a predetermined range of voltages, e.g., about 3V (140) in a range of about 6V to about 0.1V. After the first pacing pulse is delivered to the left ventricle, electrical sensing module 86 (FIG. 3) and capture detection module 90 (FIG. 3) determine if depolarization occurred in the right ventricle of the heart within a time interval that is less than an intrinsic AV interval (142), as described in detail above.

If electrical sensing module 86 (FIG. 3) and capture detection module 90 (FIG. 3) determine that depolarization did not occur at the first voltage, e.g., about 3V, within the threshold time interval ("NO" branch at 142), then processor 80 (FIG. 3) sets a stop voltage to one step higher than the initial voltage, e.g., 3.5V (144). Processor 80 (FIG. 3) increases the voltage, e.g., to a maximum value within the predetermined range of values, and controls signal generator 84 (FIG. 3) to iteratively decrement the LV pacing pulse amplitude from the maximum voltage (146). That is, signal generator 84 delivers a pacing pulse to the left ventricle at the increased voltage, e.g., about 6V. If depolarization occurred at the increased voltage, then, through a range of voltages between the maximum voltage and the first voltage, processor 80 (FIG. 3) controls signal generator 84 (FIG. 3) to iteratively decrease the voltage and deliver one or more additional pacing pulse to the left ventricle at one of the voltages in the range of voltages between the maximum voltage and the first voltage until depolarization occurs in the right ventricle within the time interval. For example, additional pacing pulse(s) of about 5V may be delivered. If depolarization occurs, additional pacing pulse(s) of about 4V may be delivered. If depolarization occurs at the pacing pulse(s) of 4V, then the amplitude of the pacing pulse may be decreased, e.g., to about 3.5V. If depolarization did not occur at 5V, then loss of capture is declared and recorded.

If there is evidence that the pacing pulse captured ("YES" branch at 142), e.g., as determined by the LVP-RVS conduction times and/or by detection of an evoked response in the LV, then capture detection module 90 selects another voltage at which to deliver a pacing pulse, using the same vector, to the left ventricle of the patient's heart that is less than the initial voltage. Capture detection module 90 also selects a minimum voltage within the range of voltages below which pacing pulses will not be delivered (148). For example, capture detection module 90 may select a voltage of about 2V at which to deliver the next pacing pulse and select a minimum voltage of 0V. Processor 80 (FIG. 3) decreases the voltage from the initial voltage, e.g., about 3V, and controls signal generator 84 (FIG. 3) to iteratively decrement the LV pacing pulse amplitude from the initial voltage (150). That is, processor 80 controls signal generator 84 to pace the RA and, at a predetermined time after the pacing pulse to the RA is delivered, timer module 96 and processor 80 control signal generator 84 to deliver a LV-only pacing pulse (LVP) via the selected vector. Again, the pacing capture threshold test is attempting to determine the minimum voltage that will capture, which will reduce power consumption and extend battery life.

If there is evidence that the pacing pulse captured, then capture detection module 90 selects another voltage at which to deliver a pacing pulse, using the same vector, to the left ventricle of the patient's heart that is less than the previous voltage. For example, capture detection module 90 may select a voltage of about 1V at which to deliver the next pacing pulse. Using the previously selected vector, processor 80 controls signal generator 84 to pace the RA and, at a predetermined time after the pacing pulse to the RA is delivered, timer module 96 and processor 80 control signal generator 84 to deliver a LV-only pacing pulse (LVP) via the selected vector.

The capture/loss of capture techniques described above may be used for each of one or more vectors. For example, if a single quadripolar lead is used to deliver stimulation, then all sixteen vectors may be tested for pacing capture thresholds. In one example, the method may include receiving user input specifying the one or more vectors to be tested.

In some examples, the first voltage is approximately within the middle of the predetermined range of voltages. In one example, the vector and a voltage at which depolarization did not occur may displayed, e.g., via a display on programmer 24. In another example, processor 80 may control the measurement of an impedance associated with the vector and control display of the impedance associated with the vector e.g., on a display of programmer 24.

In one example, the method may include determining whether capture has occurred based on the LVP-RVS conduction times, as described above, as well as the evoked response in the LV. As such declaring loss of capture may further include measuring an evoked response time and an evoked response amplitude in the left ventricle, and determining whether capture occurred based on the measured evoked response time and the evoked response amplitude.

FIG. 8 is functional block diagram illustrating an example configuration of programmer 24. As shown in FIG. 8, programmer 24 may include a processor 110, memory 112, user interface 114, telemetry module 116, and power source 118. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 114, which may include display to present graphical user interface to a user, and a keypad or another mechanism for receiving input from a user. The user, e.g., a clinician, may define or select vectors to be tested and/or input vector impedance values via user interface 114.

User interface 114 may display the vectors to be tested as well as the results of the pacing capture threshold tests to the clinician. As described above, user interface 114 may display each vector tested, and its associated pacing capture threshold voltage, in some order that the clinician may select or adjust. In some example, the impedance of each tested vector may also be displayed. The results of the tests may also be stored within memory 112.

Processor 110 can take the form one or more microprocessors, DSPs, ASICs, FPGAs, programmable logic circuitry, or the like, and the functions attributed to processor 110 herein may be embodied as hardware, firmware, software or any combination thereof. Memory 112 may store instructions that cause processor 110 to provide the functionality ascribed to programmer 24 herein, and information used by processor 110 to provide the functionality ascribed to programmer 24 herein. Memory 112 may include any fixed or removable magnetic, optical, or electrical media, such as RAM, ROM, CD-ROM, hard or floppy magnetic disks, EEPROM, Flash memory, or the like. Memory 112 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 116, which may be coupled to an internal antenna or an external antenna. An external antenna that is coupled to programmer 24 may correspond to the programming head that may be placed over heart 12, as described above with reference to FIG. 1. Telemetry module 116 may be similar to telemetry module 88 of IMD 16 (FIG. 3).

Telemetry module 116 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 110 of programmer 24 and/or one or more processors of one or more networked computers may perform all or a portion of the techniques described herein with respect to processor 80 and IMD 16. For example, processor 110 or another processor may receive voltages or currents measured by IMD 16 to calculate impedance measurements, or may receive impedance measurements from IMD 16. Processor 110 or another processor may determine LVP-RVS conduction times using any of the techniques described in this disclosure. Power source 118 delivers operating power to the components of programmer 24.

Figure 9:
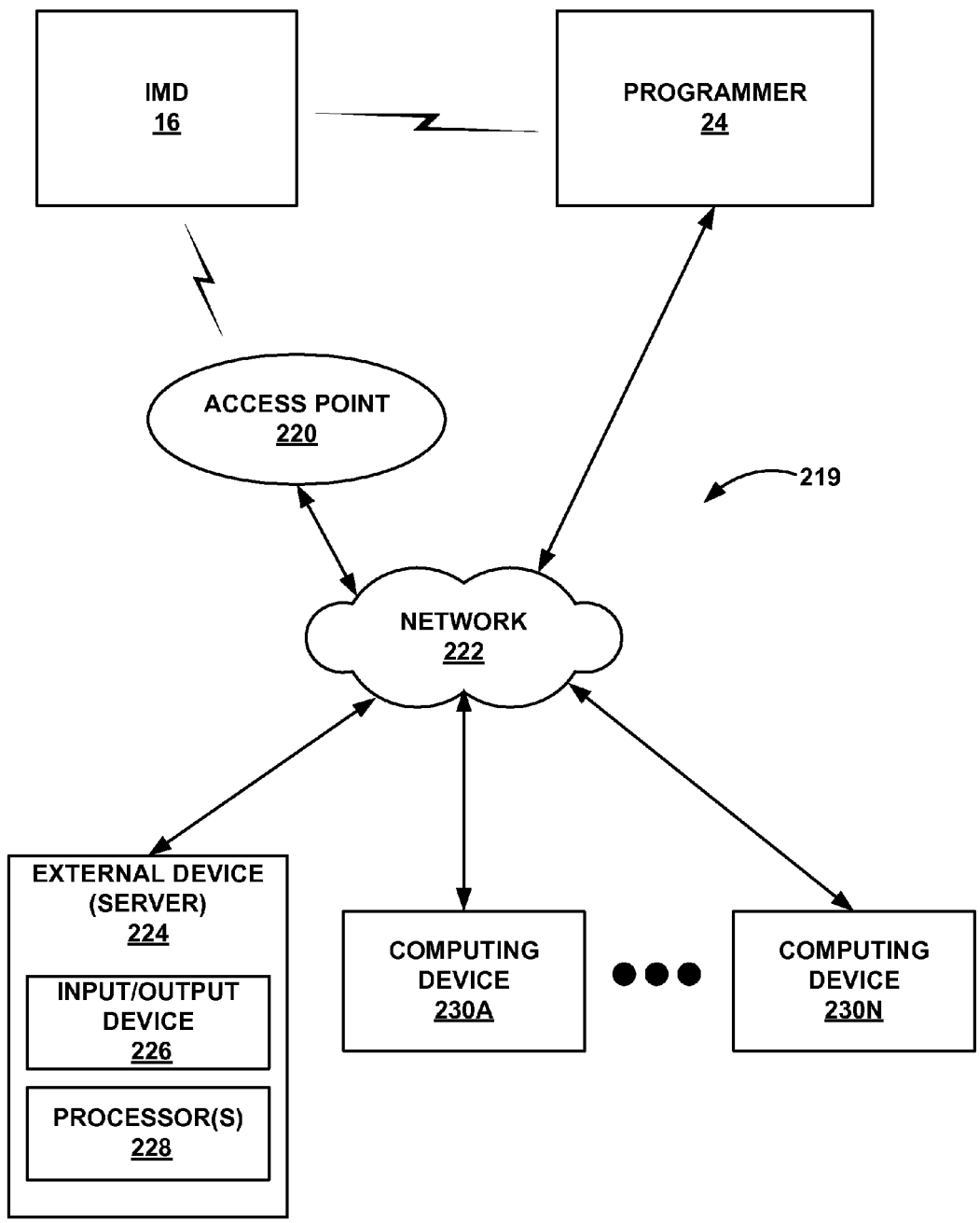
FIG. 9 is a block diagram illustrating an example system that includes a server and one or more computing devices that are coupled to the IMD and the programmer shown in FIG. 1 via a network.

FIG. 9 is a block diagram illustrating an example system 219 that includes an external device, such as a server 224, and one or more computing devices 230A-230N, that are coupled to the IMD 16 and programmer 24 shown in FIG. 1 via a network 222. In this example, IMD 16 may use its telemetry module 88 to communicate with programmer 24 via a first wireless connection, and to communication with an access point 220 via a second wireless connection. In the example of FIG. 9, access point 220, programmer 24, server 224, and computing devices 230A-230N are interconnected, and able to communicate with each other, through network 222. In some cases, one or more of access point 220, programmer 24, server 224, and computing devices 230A-230N may be coupled to network 222 through one or more wireless connections. IMD 16, programmer 24, server 224, and computing devices 230A-230N may each comprise one or more processors, such as one or more microprocessors, DSPs, ASICs, FPGAs, programmable logic circuitry, or the like, that may perform various functions and operations, such as those described herein.

Access point 220 may comprise a device that connects to network 222 via any of a variety of connections, such as telephone dial-up, digital subscriber line (DSL), or cable modem connections. In other examples, access point 220 may be coupled to network 222 through different forms of connections, including wired or wireless connections. In some examples, access point 220 may be co-located with patient 14 and may comprise one or more programming units and/or computing devices (e.g., one or more monitoring units) that may perform various functions and operations described herein. For example, access point 220 may include a home-monitoring unit that is co-located with patient 14 and that may monitor the activity of IMD 16.

In some cases, server 224 may be configured to provide a secure storage site for data that has been collected from IMD 16 and/or programmer 24. Network 222 may comprise a local area network, wide area network, or global network, such as the Internet. In some cases, programmer 24 or server 224 may assemble data in web pages or other documents for viewing by trained professionals, such as clinicians, via viewing terminals associated with computing devices 230A-230N. The illustrated system of FIG. 9 may be implemented, in some aspects, with general network technology and functionality similar to that provided by the Medtronic CareLink® Network developed by Medtronic, Inc., of Minneapolis, Minn.

In some examples, processor 228 of server 224 may be configured to receive voltages or currents measured by IMD 16 to calculate impedance measurements, or may receive impedance measurements from IMD 16. Processor 228 may determine LVP-RVS conduction times using any of the techniques described in this disclosure. Server 224 also includes input/output device 226.

Various examples of the disclosure have been described. These and other examples are within the scope of the following claims.

The invention claimed is:

1. A method of facilitating selection of at least one vector from among a plurality of vectors for pacing a first chamber of a heart, the method comprising:

for each of the plurality of vectors:
iteratively delivering, by an implantable medical device controlled by a capture detection module, at least one pacing stimulus at each of a plurality of magnitudes within a predetermined range of magnitudes to the first chamber;

for each of the plurality of pacing stimuli, determining, by the capture detection module, if a depolarization occurred in a second chamber of the heart within a predetermined threshold time interval after the pacing stimulus that is less than an intrinsic atrioventricular (AV) interval;

identifying, by the capture detection module, a pacing stimulus for which a depolarization in the second chamber does not occur within the predetermined threshold time interval;

determining, by the capture detection module, a capture threshold magnitude for the vector based on a magnitude of the pacing pulse for which a depolarization in the second chamber does not occur within the predetermined threshold time interval; and recording, by the capture detection module, the capture threshold magnitudes for the plurality of vectors of the at least one of the plurality of vectors based on the capture threshold magnitudes.

2. The method of claim 1, wherein the predetermined range of magnitudes comprises a first magnitude and a maximum magnitude, the method further comprising:
if depolarization did not occur in the second chamber within the predetermined threshold time interval, then:
increasing the first magnitude to the maximum magnitude,
through a range of magnitudes between the maximum magnitude and the first magnitude, iteratively decreasing the maximum magnitude and delivering a third pacing pulse to the first chamber at one magnitude in the range of magnitudes between the maximum magnitude and the first magnitude until depolarization occurs in the second chamber within the predetermined threshold time interval, and
declaring capture if depolarization occurs in the second chamber.

3. The method of claim 1, wherein the first chamber is a left ventricle, wherein the second chamber is a right ventricle, and wherein the at least one pacing stimulus is a voltage stimulus.

4. The method of claim 1, further comprising:
presenting the capture threshold magnitudes of the plurality of vectors.

5. The method of claim 1, further comprising:
ordering the plurality of vectors based on the capture threshold magnitudes.

6. The method of claim 1, further comprising:
selecting the at least one vector based on the capture threshold magnitudes.

7. The method of claim 1, wherein the predetermined threshold time interval is based on either the intrinsic AV interval or a time between a pacing stimulus delivered to the first chamber having a magnitude of zero and a depolarization in the second chamber.

8. The method of claim 1, wherein the first magnitude is approximately within a middle of the predetermined range of magnitudes.

9. The method of claim 1, further comprising:
for at least one of the plurality of vectors, measuring an impedance associated with the at least one of the plurality of vectors and displaying the impedance associated with the at least one vector.

10. The method of claim 1, further comprising:
measuring an evoked response time and an evoked response amplitude in the first chamber; and
determining whether capture occurred based on the evoked response time and the evoked response amplitude.

11. The method of claim 1, further comprising:
receiving user input specifying the plurality of vectors.

12. A system that facilitates selection of at least one vector from among a plurality of vectors for pacing a first chamber of a heart, the system comprising:
an implantable medical device configured to deliver pacing stimuli to the heart; and
a capture detection module that, for each of the plurality of vectors:
controls an implantable medical device to iteratively deliver at least one pacing stimulus at each of a plurality of magnitudes within a predetermined range of magnitudes to the first chamber;
for each of the plurality of pacing stimuli, determines if a depolarization occurred in a second chamber of the heart within a predetermined threshold time interval after the pacing stimulus that is less than an intrinsic atrioventricular (AV) interval;
identifies a pacing stimulus for which a depolarization in the second chamber does not occur within the predetermined threshold time interval; and
determines a capture threshold magnitude for the vector based on a magnitude of the pacing stimulus for which a depolarization in the second chamber does not occur within the predetermined threshold time interval,
wherein the capture detection module records the capture threshold magnitudes for the plurality of vectors for selection of one of the plurality of vectors based on the capture threshold magnitudes.

13. The system of claim 12, wherein the predetermined range of magnitudes comprises a first magnitude and a maximum magnitude, and if depolarization did not occur in the second chamber within the predetermined threshold time interval, then the capture detection module controls the implantable medical device to:
increase the first magnitude to the maximum magnitude,
through a range of magnitudes between the maximum magnitude and the first magnitude, iteratively decrease the maximum magnitude and deliver a third pacing pulse to the first chamber at one magnitude in the range of magnitudes between the maximum magnitude and the first magnitude until depolarization occurs in the second chamber within the predetermined threshold time interval, and
declare capture if depolarization occurs in the second chamber.

14. The system of claim 12, wherein the first chamber is a left ventricle, wherein the second chamber is a right ventricle, and wherein the at least one pacing stimulus is a voltage stimulus.

15. The system of claim 12, wherein the capture detection module controls the implantable medical device to:
present the capture threshold magnitudes of the plurality of vectors.

16. The system of claim 12, wherein the capture detection module controls the implantable medical device to:
order the plurality of vectors based on the capture threshold magnitudes.

17. The system of claim 12, wherein the capture detection module controls the implantable medical device to:
select the at least one vector based on the capture threshold magnitudes.

18. The system of claim 12, wherein the predetermined threshold time interval is based on either the intrinsic AV interval or a time between a pacing stimulus delivered to the first chamber having a magnitude of zero and a depolarization in the second chamber.

19. The system of claim 12, wherein the first magnitude is approximately within a middle of the predetermined range of magnitudes.

20. The system of claim 12, wherein the capture detection module controls the implantable medical device to:
for at least one of the plurality of vectors, measure an impedance associated with the at least one of the plurality of vectors and display the impedance associated with the at least one vector.

21. The system of claim 12, wherein the capture detection module controls the implantable medical device to:
measure an evoked response time and an evoked response amplitude in the first chamber; and
determine whether capture occurred based on the evoked response time and the evoked response amplitude.

22. The system of claim 12, a user interface for receiving user input specifying the plurality of vectors.

23. A computer-readable storage medium comprising instructions that, when executed by a processor, cause the processor to:
control an implantable medical device to iteratively deliver, for each of a plurality of vectors, at least one pacing stimulus at each of a plurality of magnitudes within a predetermined range of magnitudes to a first chamber;
for each of the pacing stimuli, determine if a depolarization occurred in a second chamber of the heart within a predetermined threshold time interval after the pacing stimulus that is less than an intrinsic atrioventricular (AV) interval;
identify a pacing stimulus for which a depolarization in the second chamber does not occur within the predetermined threshold time interval; and
determine a capture threshold magnitude for a respective vector based on the magnitude of the pacing stimulus for which a depolarization in the second chamber does not occur within the predetermined threshold time interval,
wherein the processor records the respective capture threshold magnitudes for each of the plurality of vectors for selection of one of the vectors based on the capture threshold magnitudes.

24. A system comprising:
for each of one or more vectors, means for delivering a first pacing pulse having a first voltage within a predetermined range of voltages to a left ventricle of a heart, the range of voltages having a maximum voltage and a minimum voltage;
means for determining if depolarization occurred in a right ventricle of the heart within a time interval;
if depolarization occurred in the right ventricle within the time interval, then:
through a first range of voltages between the first voltage and the minimum voltage, means for iteratively decreasing the first voltage and delivering a second pacing pulse to the left ventricle at one voltage in the first range of voltages until depolarization does not occur in the right ventricle within the time interval, and
means for declaring loss of capture of the right ventricle if depolarization does not occur in the right ventricle; and
if depolarization did not occur in the right ventricle within the time interval, then:
means for increasing the first voltage to the maximum voltage,
through a second range of voltages between the maximum voltage and the first voltage, means for iteratively decreasing the maximum voltage and delivering a third pacing pulse to the left ventricle at one voltage in the second range of voltages until depolarization occurs in the right ventricle within the time interval, and
means for declaring capture of the right ventricle if depolarization occurs in the right ventricle.

25. The system of claim 17, wherein the capture detection module controls the implantable medical device to:
select the at least one vector having the lowest capture threshold magnitude of the capture threshold magnitudes.

* * * * *